US012111303B2

(12) United States Patent
Demieville et al.

(10) Patent No.: US 12,111,303 B2
(45) Date of Patent: *Oct. 8, 2024

(54) SYSTEM AND METHOD FOR DETERMINING A LOCATION OF ORE IN A STOCKPILE

(71) Applicant: FREEPORT MINERALS CORPORATION, Phoenix, AZ (US)

(72) Inventors: Cory A. Demieville, Scottsdale, AZ (US); Dana Geislinger, Chandler, AZ (US); Travis Gaddie, Phoenix, AZ (US); Margaret Alden Tinsley, Titusville, FL (US); Muneeb Alam, Alexandria, VA (US); Steven Chad Richardson, Thatcher, AZ (US); Akaash Sanyal, Boston, MA (US); Raquel Crossman, Mesa, AZ (US); Tianfang Ni, Boston, MA (US); Luke Gerdes, Framingham, MA (US); Robyn Freeman, Menlo Park, CA (US); Oleksandr Klesov, Lexington, MA (US); Luciano Kiniti Issoe, Sao Paulo (BR)

(73) Assignee: FREEPORT MINERALS CORPORATION, Phoenix, AZ (US)

( * ) Notice: Subject to any disclaimer, the term of this patent is extended or adjusted under 35 U.S.C. 154(b) by 273 days.

This patent is subject to a terminal disclaimer.

(21) Appl. No.: 17/850,866

(22) Filed: Jun. 27, 2022

(65) Prior Publication Data

US 2023/0417724 A1  Dec. 28, 2023

(51) Int. Cl.
*G01N 33/24* (2006.01)
*G01N 15/0227* (2024.01)

(52) U.S. Cl.
CPC ......... *G01N 33/24* (2013.01); *G01N 15/0227* (2013.01)

(58) Field of Classification Search
CPC ...................................................... G01N 33/24
See application file for complete search history.

(56) References Cited

U.S. PATENT DOCUMENTS 6,319,389 B1 11/2001 Fountain et al.
8,986,423 B2  3/2015 Lang et al.
(Continued)

FOREIGN PATENT DOCUMENTS

CA    2573936    5/2010
CA    3059069    8/2021
(Continued)

OTHER PUBLICATIONS

CN113223158A English translated version, abstract, (Aug. 6, 2021).*
(Continued)

*Primary Examiner* — Hyun D Park
(74) *Attorney, Agent, or Firm* — SNELL & WILMER L.L.P.

(57) ABSTRACT

The method may comprise receiving historical data (e.g., mineralogy data, irrigation data, raffinate data, heat data, lift height data, geographic data on ore placement and/or blower data); training a predictive model using the historical data to create a trained predictive model; adding future assumption data to the trained predictive model; running the forecast engine for a plurality of parameters to obtain forecast data for a mining production target; comparing the forecast data for the mining production target to the actual data for the mining production target; determining deviations between the forecast data and the actual data, based on the comparing; and changing each of the plurality of parameters from (Continued)

the forecast data to the actual data to determine a contribution to the deviations for each of the plurality of parameters.

20 Claims, 13 Drawing Sheets

(56) References Cited

U.S. PATENT DOCUMENTS

| | | | |
|---|---|---|---|
| 9,593,463 | B1 | 3/2017 | Hiranaka |
| 10,235,566 | B2 | 3/2019 | Alvarez Gonzalez et al. |
| 11,354,013 | B1 | 6/2022 | Nivon et al. |
| 11,521,138 | B1 | 12/2022 | Geislinger et al. |
| 11,681,959 | B1 | 6/2023 | Geislinger et al. |
| 11,823,099 | B1 | 11/2023 | Issoe et al. |
| 11,893,519 | B2 | 2/2024 | Geislinger et al. |
| 11,948,103 | B2 | 4/2024 | Geislinger et al. |
| 2005/0071258 | A1 | 3/2005 | Kumakawa |
| 2005/0136527 | A1 | 6/2005 | Buuren |
| 2005/0183930 | A1 | 8/2005 | Bernard et al. |
| 2005/0211019 | A1 | 9/2005 | Crundwell et al. |
| 2007/0169587 | A1 | 7/2007 | Dekock et al. |
| 2008/0023342 | A1 | 1/2008 | Marsden et al. |
| 2008/0156656 | A1 | 7/2008 | Marsden et al. |
| 2009/0216410 | A1 | 8/2009 | Allen et al. |
| 2009/0230207 | A1 | 9/2009 | Guzman et al. |
| 2009/0319310 | A1 | 12/2009 | Little |
| 2011/0129891 | A1 | 6/2011 | Plessis |
| 2012/0001474 | A1* | 1/2012 | Stokes ............... E21C 41/26 299/10 |
| 2012/0084047 | A1 | 4/2012 | Vesterdal et al. |
| 2012/0173185 | A1 | 7/2012 | Taylor et al. |
| 2012/0187286 | A1 | 7/2012 | Auranen et al. |
| 2012/0297928 | A1 | 11/2012 | Lang et al. |
| 2014/0214235 | A1 | 7/2014 | Kini et al. |
| 2014/0291499 | A1 | 10/2014 | Mathieu |
| 2014/0318530 | A1 | 10/2014 | Gerpheide |
| 2014/0367899 | A1 | 12/2014 | Cramer |
| 2015/0082943 | A1 | 3/2015 | Cartagena Fagerstrom et al. |
| 2015/0154703 | A1 | 6/2015 | Rohlfs |
| 2015/0167117 | A1 | 6/2015 | Brueggemann et al. |
| 2015/0193691 | A1* | 7/2015 | Silversides ............ G01V 5/06 706/11 |
| 2015/0225809 | A1 | 8/2015 | Robertson et al. |
| 2016/0003009 | A1 | 1/2016 | Oppolzer |
| 2016/0019792 | A1 | 1/2016 | Kawamata et al. |
| 2016/0068977 | A1 | 3/2016 | Robertson et al. |
| 2016/0153070 | A1 | 6/2016 | Duyvesteyn |
| 2016/0196699 | A1 | 7/2016 | Chitty et al. |
| 2016/0258036 | A1 | 9/2016 | Rautenback |
| 2017/0297067 | A1 | 10/2017 | Lagenbeck |
| 2018/0074201 | A1 | 3/2018 | Sakai et al. |
| 2018/0150779 | A1 | 5/2018 | Wei |
| 2019/0026531 | A1 | 1/2019 | Gonzalez et al. |
| 2019/0180627 | A1 | 6/2019 | Talmaki et al. |
| 2019/0284657 | A1 | 9/2019 | Robertson et al. |
| 2019/0302794 | A1 | 10/2019 | Kean et al. |
| 2020/0011175 | A1 | 1/2020 | Gates |
| 2020/0034879 | A1 | 1/2020 | Wai |
| 2020/0064145 | A1 | 2/2020 | McAlpine et al. |
| 2020/0264573 | A1 | 8/2020 | Baldrey |
| 2020/0340077 | A1 | 10/2020 | Lizama et al. |
| 2021/0047804 | A1 | 2/2021 | Canepari |
| 2021/0099828 | A1 | 4/2021 | Hanna et al. |
| 2021/0156810 | A1 | 5/2021 | Botto et al. |
| 2021/0248841 | A1 | 8/2021 | Helms et al. |
| 2021/0398157 | A1 | 12/2021 | Aras et al. |
| 2022/0113725 | A1 | 4/2022 | Vandike et al. |
| 2022/0275475 | A1 | 9/2022 | Singh et al. |
| 2023/0038474 | A1 | 2/2023 | Miljak et al. |
| 2023/0112842 | A1 | 4/2023 | Rendahl et al. |
| 2023/0123961 | A1 | 4/2023 | Morizane et al. |
| 2023/0417552 | A1 | 12/2023 | Issoe et al. |
| 2023/0417570 | A1 | 12/2023 | Geislinger et al. |
| 2023/0418269 | A1 | 12/2023 | Richardson et al. |
| 2023/0419132 | A1 | 12/2023 | Issoe et al. |
| 2023/0419197 | A1 | 12/2023 | Geislinger et al. |
| 2023/0419198 | A1 | 12/2023 | Geislinger et al. |
| 2023/0419199 | A1 | 12/2023 | Geislinger et al. |
| 2023/0419226 | A1 | 12/2023 | Klesov et al. |
| 2023/0419249 | A1 | 12/2023 | Gaddie et al. |
| 2024/0037462 | A1 | 2/2024 | Geislinger et al. |

FOREIGN PATENT DOCUMENTS

| | | | |
|---|---|---|---|
| CN | 113223158 A | * 8/2021 | ............ G06T 17/00 |
| WO | WO2009146485 | 12/2009 | |
| WO | WO2011068859 | 6/2011 | |
| WO | WO2021127735 | 7/2021 | |
| WO | WO2024006200 | 1/2024 | |
| WO | WO2024006208 | 1/2024 | |
| WO | WO2024006214 | 1/2024 | |
| WO | WO2024006215 | 1/2024 | |
| WO | WO2024006217 | 1/2024 | |
| WO | WO2024006219 | 1/2024 | |
| WO | WO2024006683 | 1/2024 | |
| WO | WO2024006684 | 1/2024 | |
| WO | WO2024006686 | 1/2024 | |
| WO | WO2024006687 | 1/2024 | |
| WO | WO2024006689 | 1/2024 | |

OTHER PUBLICATIONS

USPTO Non Final Office Action from U.S. Appl. No. 18/485,143 dated Dec. 22, 2023.
US Enviornmental Protection Agency, Office of Solid Waste, Special Waste Branch, Acid Generation Prediction in Mining, US Environmental, 1993.
R. Mathur, W.J. Schlitt, Identification of the dominant Cu ore minerals providing soluble copper at Canariaco, Peru through Cu isotope analyses of batch leach experiments, Hydrometallurgy 101 (2010) 15-19.
Robert D. Henderson, Minera Valle Central Operation, Rancagua, Region VI, Chile, 43-101 Techical Report, amerigoresources.com, effective date: Dec. 31, 2013, RDHP Eng-amerigoresources.com.
D. Baron van Wassenaer, The reprocessing of historic mine tailings, Aalto University School of Chemical Engineering, 2021—aaltodoc. aalto.fi.
Response to USPTO Final Office Action from U.S. Appl. No. 18/306,640 dated Jan. 31, 2024.
USPTO Final Office Action from U.S. Appl. No. 18/485,143 dated Mar. 15, 2024.
S. Yin, Y. Shao, A. Wu, H. Wang, X. Liu, Y. Wang, A Systematic Review of Paste Technology in Metal Mines for Cleaner Production in China, Journal of Cleaner Production, 2020—Elsevier, 2020.
USPTO Non-Final Office Action from U.S. Appl. No. 17/850,880 dated Mar. 20, 2024.
USPTO Notice of Allowance from U.S. Appl. No. 17/850,834 dated Sep. 29, 2022.
USPTO Non-Final Office Action from U.S. Appl. No. 17/985,446 dated Jan. 26, 2023.
Reply to Office Action and Amendment from U.S. Appl. No. 17/985,446 dated Feb. 7, 2023.
Examiner Interview Summary from U.S. Appl. No. 17/985,446 dated Feb. 8, 2023.
Terminal Disclaimer from U.S. Appl. No. 17/985,446 dated Mar. 3, 2023.
USPTO Notice of Allowance from U.S. Appl. No. 17/985,446 dated Mar. 9, 2023.
PCT Notification of Transmittal of the International Search Report and the Written Opinion of the International Searching Authority with International Search Report and Written Opinion from PCT/US2023/026217 dated Jul. 27, 2023.
USPTO Non-Final Office Action from U.S. Appl. No. 18/306,534 dated Aug. 21, 2023.
USPTO Non-Final Office Action from U.S. Appl. No. 18/306,640 dated Sep. 6, 2023.
PCT Notification of Transmittal of the International Search Report and the Written Opinion of the International Searching Authority

(56) References Cited

OTHER PUBLICATIONS with International Search Report and Written Opinion from PCT/US2023/026249 dated Sep. 12, 2023.
Kumcu. "Column Test and Heap Leach Modeling." Published May 9, 2022.
Young et al. "Modelling Large Heaped Fill Stockpiles Using FMS Data." Jun. 15, 2021.
USPTO Non-Final Office Action from U.S. Appl. No. 18/339,998 dated Sep. 28, 2023.
USPTO Notice Of Allowance from U.S. Appl. No. 18/306,749 dated Sep. 27, 2023.
PCT Notification of Transmittal of the International Search Report and the Written Opinion of the International Searching Authority with International Search Report and Written Opinion from PCT/US2023/026242 dated Sep. 29, 2023.
PCT Notification of Transmittal of the International Search Report and the Written Opinion of the International Searching Authority with International Search Report and Written Opinion from PCT/US2023/026228 dated Sep. 29, 2023.
PCT Notification of Transmittal of the International Search Report and the Written Opinion of the International Searching Authority with International Search Report and Written Opinion from PCT/US2023/026235 dated Oct. 16, 2023.
PCT Notification of Transmittal of the International Search Report and the Written Opinion of the International Searching Authority with International Search Report and Written Opinion from PCT/US2023/069051 dated Oct. 18, 2023.
PCT Notification of Transmittal of the International Search Report and the Written Opinion of the International Searching Authority with International Search Report and Written Opinion from PCT/US2023/069052 dated Oct. 18, 2023.
Barrena et al. "Prediction of temperature and thermal inertia effect in the maturation stage and stockpiling of a large composting mass." In: Waste Management 26 (2006) 953-959, Oct. 4, 2005, https://www.sciencedirect.com/science/article/pii/S0956053X05002205.
PCT Notification of Transmittal of the International Search Report and the Written Opinion of the International Searching Authority with International Search Report and Written Opinion from PCT/US2023/026246 dated Oct. 24, 2023.
USPTO Notice Of Allowance from U.S. Appl. No. 18/306,534 dated Nov. 8, 2023.
PCT Notification of Transmittal of the International Search Report and the Written Opinion of the International Searching Authority with International Search Report and Written Opinion from PCT/US2023/069047 dated Nov. 16, 2023.
PCT Notification of Transmittal of the International Search Report and the Written Opinion of the International Searching Authority with International Search Report and Written Opinion from PCT/US2023/069046 dated Nov. 16, 2023.
Qinghua et al. "Dynamic management system of ore blending in an open pit mine based on GIS/GPS/GPRS." Mining Science and Technology (China), vol. 20, Issue 1, Jan. 2010.
Lee et al. "Utilization analysis methodology for fleet telematics of heavy earthwork equipment." Automation in Construction, vol. 92, Aug. 2018.
Reply to Written Opinion, PCT Demand and Letter Accompanying Amendment Under Article 19 as filed with the USPTO from PCT/US2023/026249 dated Nov. 9, 2023.
Letter Accompanying Amendment Under Article 19 as filed with the IB from PCT/US2023/026249 dated Nov. 9, 2023.
Reply to Written Opinion, PCT Demand and Letter Accompanying Amendment Under Article 19 as filed with the USPTO from PCT/US2023/026242 dated Nov. 21, 2023.
Letter Accompanying Amendment Under Article 19 as filed with the IB from PCT/US2023/026242 dated Nov. 21, 2023.
Reply to Written Opinion, PCT Demand and Letter Accompanying Amendment Under Article 19 as filed with the USPTO from PCT/US2023/026228 dated Nov. 27, 2023.
Letter Accompanying Amendment Under Article 19 as filed with the IB from PCT/US2023/026228 dated Nov. 27, 2023.
Reply to Written Opinion, PCT Demand and Letter Accompanying Amendment Under Article 19 as filed with the USPTO from PCT/US2023/026235 dated Dec. 6, 2023.
Letter Accompanying Amendment Under Article 19 as filed with the IB from PCT/US2023/026235 dated Dec. 6, 2023.
Reply to Written Opinion, PCT Demand and Letter Accompanying Amendment Under Article 19 as filed with the USPTO from PCT/US2023/069051 dated Dec. 8, 2023.
Letter Accompanying Amendment Under Article 19 as filed with the IB from PCT/US2023/069051 dated Dec. 8, 2023.
Reply to USPTO Non-Final Office Action from U.S. Appl. No. 18/306,534 dated Oct. 25, 2023.
Reply to USPTO Non-Final Office Action from U.S. Appl. No. 18/339,998 dated Oct. 17, 2023.
USPTO Non-Final Office Action from U.S. Appl. No. 18/339,998 dated Nov. 21, 2023.
Reply to USPTO Non-Final Office Action from U.S. Appl. No. 18/306,640 dated Nov. 21, 2023.
USPTO Final Office Action from U.S. Appl. No. 18/306,640 dated Dec. 12, 1023.
Reply to Non-Final Office Action from U.S. Appl. No. 18/339,998 dated Dec. 13, 2023.
Reply to Written Opinion, PCT Demand and Letter Accompanying Amendment Under Article 19 as filed with the USPTO from PCT/US2023/069052 dated Dec. 12, 2023.
Letter Accompanying Amendment Under Article 19 as filed with the IB from PCT/US2023/069052 dated Dec. 12, 2023.
Reply to Written Opinion, PCT Demand and Letter Accompanying Amendment Under Article 19 as filed with the USPTO from PCT/US2023/069055 dated Dec. 12, 2023.
Letter Accompanying Amendment Under Article 19 as filed with the IB from PCT/US2023/069055 dated Dec. 12, 2023.
Reply to Written Opinion, PCT Demand and Letter Accompanying Amendment Under Article 19 as filed with the USPTO from PCT/US2023/026246 dated Dec. 12, 2023.
Letter Accompanying Amendment Under Article 19 as filed with the IB from PCT/US2023/026246 dated Dec. 12, 2023.
Posted by Paul Moore, "Anglo American utilising latest digital twin technology at Quellaveco," International Mining, https://im-mining.com, Dec. 12, 2022.
Heap Leach Modeling—A Review of Approaches to Metal Production Forecasting, J.O. Marsden, M.M. Botz, Minerals & Metallurgical Processing, 2017, vol. 34 No. 2, pp. 53-64.
USPTO Non Final Office Action from U.S. Appl. No. 17/850,884 dated Apr. 9, 2024.
Response to Final Office Action with AFCP Request from U.S. Appl. No. 18/485,143 dated Apr. 10, 2024.
USPTO Advisory Action, Inverview Summary and Decision on AFCP Request from U.S. Appl. No. 18/485,143 dated Apr. 19, 2024.
Response to Advisory Action with RCE from U.S. Appl. No. 18/485,143 dated Apr. 19, 2024.
USPTO Advisory Action, Inverview Summary and Decision on AFCP Request from U.S. Appl. No. 18/306,640 dated Apr. 23, 2024.
Response to Advisory Action with RCE from U.S. Appl. No. 18/306,640 dated Apr. 23, 2024.
PCT International Preliminary Report on Patentability from PCT/US2023/026249 dated Apr. 19, 2024.
USPTO Non Final Office Action from U.S. Appl. No. 17/850,864 dated Apr. 25, 2024.
PCT International Report on Preliminary Patentability from PCT/US2023/026235 dated Apr. 22, 2024.
USPTO Non Final Office Action from U.S. Appl. No. 17/850,894 dated Jul. 19, 2024.
Choi et al "Review of GIS-Based Applications for Mining: Planning, Operation, and Environmental Management", Applied Sciences, 10(7) 2266 (Year 2020).
USPTO Non Final Office Action in U.S. Appl. No. 18/398,613 dated May 22, 2024.
Dale F. Rucker, Shawn Calendine. "Secondary recovery of a copper heap leach", 2014, InfoMine, Heap Leach Solutions (Year 2014).
Tim T. Werner, Gavin M. Mudd, Aafke M. Schipper, Mark A.J. Huijbregts, Lakshay Taneja, Stephen A. Northey, Global-scale remote

(56) References Cited

OTHER PUBLICATIONS sensing of mine areas and analysis of factors explaining their extent: 2020, Global Environmental Change, vol. 60, 102007 (Year 2020).
USPTO Non Final Office Action in U.S. Appl. No. 18/433,776 dated Jun. 20, 2024.

* cited by examiner

| Model Feature | Description | Units | Data Source | Expected Relationship with Target Variable |
|---|---|---|---|---|
| Raffinate Flow | Average daily flow rate across all irrigated sections | gal/minute | flow-meter sensors | Higher flow leads to higher production |
| Raffinate Fe | Average iron concentration in raffinate solution | g/L | reports | More total Fe available → higher production |
| Raffinate Fe³/Fe² Ratio | Ratio of ferric to ferrous iron in raffinate solution [ratio feature can differ, but there should be same comparison of Fe content in the raffinate solution (i.e. Fe³/total Fe)] | N/A | reports | Higher ratio of Ferric:Ferrous → higher production |
| Raffinate Acid | Average concentration of $H_2SO_4$ in raffinate solution | g/L | reports | Higher [acid] → higher production |
| Raffinate Cu | Average [Cu] in raffinate solution | g/L | reports | Higher [Cu] in raffinate → lower production |
| Days Under Leach | Aggregated amount of time currently irrigated sections have been under irrigation for on a given day | Days | Irrigation Data | Longer DUL → lower production (less Cu remaining to be leached) |
| TCu | Average total copper grade of material in all sections currently under irrigation on a given day (weighted by section area) | % | MMT (mapped to pile sections) | Higher TCu → higher production |
| XCu | Average acid-soluble copper grade (more easily leached Cu) of material in all sections currently under irrigation on a given day (weighted by section area) | % | MMT (mapped to pile sections) | Higher XCu → higher production |
| QLT | Average result of the QLT (quick leach test) lab assay of material in all sections currently under irrigation on a given day (weighted by section area) | % | MMT (mapped to pile sections) | Higher QLT → higher production |

FIG. 2A

| Model Feature | Description | Units | Data Source | Expected Relationship with Target Variable |
|---|---|---|---|---|
| P80 | 80th quantile SDR particle size of material in all sections currently under irrigation on a given day (weighted by section area) | inches | MMT (mapped to pile sections) | Larger P80 → lower production |
| Application Rate | Application rate is the ratio of raffinate flow: total area under irrigation on a given day | gpm/ft² | Flow data and irrigation data (area) | There exists an optimal value for application rate under which production is inhibited, but in most HELENA models we observe values greater than this optima so higher app_rate → lower production |
| Lift Height | Height of the lift for each section currently under irrigation (weighted by section area) | ft | Haul truck sensor elevation data | Higher lift heights → lower production |
| In-Pile temperature | Section temperature estimated as a soft-sensor using the heat model given inputs on section mineralogy and pile conditions | °C | Heat Model (MMT/ Irrigation inputs) | Higher temperatures → higher production |
| Blowers | Whether or not blowers are turned on by day; blower have been found to impact pile temperature | N/A | Servers | Higher production when blowers are turned on |
| Cure Acid | Additional acid added to raffinate when irrigating new lifts (only applied on some piles/lifts) | lbs. | Reports | Cure acid → higher production |

FIG. 2B

| Column 1 | Column 2 | Column 3 |
|---|---|---|
| Brakes Crackle | Rear Right Final Particle Counter for FatCum50 | Post Filter 6 Kidney Loop PQ Index for PQ |
| Center Differential FTIR for Antiwear | Right Final Particle Counter for Fibers | Post Filter 7 Kidney Loop TAN for TAN |
| Front Differential FTIR for Ester BD | Left Front Wheel Particle Counter for ISO14 | Pre Filter Kidney Loop TBN for TBN |
| ISO Test Differential FTIR for Glycol | Right Front Wheel Particle Counter for ISO4 | Pre Filter 1 Kidney Loop Viscosity 100 for Flow |
| Kidney Loop 1 Hr Differential FTIR for Hydroxy | Hydraulics Particle Counter for ISO6 | Pre Filter 2 Kidney Loop Viscosity 100 for Viscosity |
| Differential FTIR for NOx | Hydraulics Particle Counter for MDiamCum10 | Pre Filter 3 Kidney Loop Viscosity 40 for Flow |
| Differential FTIR for NOx vs Oxid | Post Filter Hydraulics Particle Counter for MDiamCum100 | Pre Filter 4 Kidney Loop Viscosity 40 for Viscosity |
| Post Filter Differential FTIR for Oxidation | Post Kidney Loop Hydraulics Particle Counter for MDiamCum15 | Pre Filter 5 Kidney Loop Water Content for H2O |
| Post Kidney Loop Differential FTIR for Soot 1980 | Pre Filter Hydraulics Particle Counter for MDiamCum20 | Pre Filter 6 Kidney Loop Wear Debris for Wear Debris |
| Pre Filter Differential FTIR for Sulfur vs Oxid | Pre Kidney Loop Hydraulics Particle Counter for MDiamCum25 | Pre Filter 7 Kidney Loop Wear Metals for Ag |
| Rear Differential FTIR for Sulfate | Post Filter Kidney Loop Particle Counter for MDiamCum5 | Mag Plug-Differential Wear Metals for Al |
| Cuff Engine, Diesel FTIR for Water | Post Filter 1 Kidney Loop Particle Counter for MDiamCum50 | Left Mag Plug-Final Wear Metals for B |
| Engine, Diesel Fuel Sniffer for Diesel Fuel | Post Filter 2 Kidney Loop Particle Counter for OxideCum100 | Right Mag Plug-Final Wear Metals for Ba |
| Engine, Diesel Magnetic Plugs for Magnetic Material | Post Filter 3 Kidney Loop Particle Counter for OxideCum20 | Left Mag Plug-Spindle Wear Metals for Ca |
| Center Left Final Particle Counter for CutCum100 | Post Filter 4 Kidney Loop Particle Counter for OxideCum25 | Mag Plug-Spindle Wear Metals for Cr |
| Center Right Final Particle Counter for CutCum20 | Post Filter 5 Kidney Loop Particle Counter for OxideCum50 | Rear Mag Plug-Spindle Wear Metals for Cu |
| Front Left Final Particle Counter for CutCum25 | | Right Mag Plug-Spindle Wear Metals for Fe |
| Front Right Final Particle Counter for CutCum50 | | Left Spindle Wear Metals for K |
| Left Final Particle Counter for FatCum100 | | Spindle Wear Metals for Mg |
| Rear Final Particle Counter for FatCum20 | | Right Spindle Wear Metals for Mn |
| Rear Left Final Particle Counter for FatCum25 | | Steering Wear Metals for Mo |

FIG. 7A

| | | |
|---|---|---|
| Steering Wear Metals for Na | Positive 15 Vdc Power Supply | PSC Not Ready Light Active |
| Torque Converter Wear Metals for Ni | Positive 5 Vdc Computer Supply | PSC Composite Temperature at Limit |
| Transfer case Wear Metals for P | Net Horsepower Feedback at Alternator input | Propulsion System State |
| Transmission Wear Metals for Pb | Negative 15 Vdc Power Supply | OEM Speed Setting 2 Output Active |
| Transmission Wear Metals for Si | Keyswitch Battery Potential | OEM Speed Setting 1 Output Active |
| Left Wheel Motor Wear Metals for Sn | DC Link Voltage | No Retard or Propel Mode Allowed |
| | DC Link On | |
| Right Wheel Motor Wear Metals for Ti | DC Link Energized Light | No Retard or Propel allowed light |
| | DC Link Current | No Propel Mode Active |
| Wear Metals for V | Cranking Battery Voltage | No propel allowed |
| Wear Metals for Zn | Battery Voltage Out of Range | Lamp Test Request Switch |
| Reverse Direction Request | Control Blower Pressure OK | Gear Select By Operator |
| PLM Data Age | | Event 20 Pre Warning Light |
| GE Data Age | Wheel 2 Slip Correction Active | |
| Forward Direction Request | Wheel 2 Slide Correction Active | Dump Override Reset Event Switch |
| Engine Data Age | | Drive System Status |
| Right Rear Wheel Speed | Wheel 1 Slip Correction Active | Control Power On |
| Right Front Wheel Speed | | Composite PSC Temperature |
| Retarder | Wheel 1 Slide Correction Active | |
| Retard System at Continuous Rating | | Axle Box Pressure Sensor |
| | Transmission Gear | Axle Box Air Pressure Sensor |
| Retard Speed Control Percent | Speed Limit Restriction Active | |
| | | Auxiliary Panel Error Code |
| Retard Mode Light Active | Reverse Mode Light Active | Inverters Status |
| Retard Continuous Light | REST Mode Request Switch | Inverter 2 Torque Feedback |
| Pre Shift Brake Test Request | | |
| Parking Brake | REST Mode Light Active | Inverter 2 Disable Fault |
| Park Brake Feedback | Request PSC to store Datapack | Inverter 1 Torque Feedback |
| Left Rear Wheel Speed | | |
| Left Front Wheel Speed | Reduced propel retard effort | Inverter 1 Limit Mode Active |
| External Retard Light Active | PSC Warning Speed Limit Light | Inverter 1 Disable Fault |
| | | Auxiliary Inverter DC Link Voltage |
| Brake Temperature | PSC TCI Communication Link | Horsepower |

FIG. 7B

| | | |
|---|---|---|
| Ground Speed Limit | GPS Snapped Longitude of Equipment | Engine Operating State |
| Ground Speed GE | | Engine Load |
| GE Uptime | GPS Snapped Latitude of Equipment | Engine Injector Timing Rail Pressure |
| GE Device Active | | |
| Engine Warning Signal | GPS Snapped Direction of Travel | Engine Injector Metering Rail Pressure |
| Engine Warmup Mode Request | | |
| | GPS Incline | Engine Idle Shutdown Timer State |
| Engine Start Request | GPS Fix Quality Number | |
| Engine Speed Setting | Gps Uptime | Engine Idle Shutdown Timer Override |
| Engine Speed Restriction and RP1 Closure | GPS Time of Equipment | |
| | GPS Satellites Tracked | Engine Idle Shutdown Timer Function |
| Engine Kill Cutoff switch | GPS Longitude of Equipment | |
| Engine Cranking Output 2 | | Engine Idle Shutdown Driver Alert Mode |
| Engine Cranking Output | GPS Latitude of Equipment | |
| Engine Caution Light | | Drivers Demand Engine Percent Torque |
| Barometric Pressure GE | GPS Heading of Equipment | |
| Swing Predicted Payload After Next Swing | | Crankcase Air Pressure Gauge |
| | GPS HDOP | |
| Swing Payload | GPS Ground Speed of Equipment | Atmospheric Pressure |
| Right Rear Suspension Cylinder | | Ambient Air Temperature |
| | GPS Fix Quality | Actual Engine Percent Torque |
| Right Front Suspension Cylinder | GPS Elevation | |
| | GPS Active | Accelerator Pedal Low Idle Switch |
| Payload Status | Throttle Position | |
| Payload | Remote Accelerator Pedal Position | Acceleration Pedal Input Request |
| Mid Level Payload Signal | | |
| Left Rear Suspension Cylinder | Nominal Friction Percent Torque | Refrigerant Low Pressure Switch |
| | Idle Shut Down Switch | Refrigerant High Pressure Switch |
| Left Front Suspension Cylinder | Engines Desired Operating Speed Asymmetry Adjustment | |
| | | Engine ECU Temperature |
| Haul Distance | | Engine Coolant Temperature |
| Ground Speed PLM | Engines Desired Operating Speed | |
| Body Position Angle | | Engine Coolant Pressure |
| Body Position | Engine Torque Mode | AC High Pressure Fan Switch |
| Body Float PLM | Engine Speed | |
| TKPHR Tires | Engine Protection System has Shutdown Engine | PLM Engine Running (Oil Pressure) |
| TKPH RF Tire | | |
| TKPH LF Tire | Engine Protection System Configuration | Engine Pre-filter Oil Pressure |
| GPS Snapped Point ID | | |
| GPS Snapped Point Confidence Level | | Engine Oil Temperature |
| | Engine Protection System Approaching Shutdown | Engine Oil Pressure Quantum |

FIG. 7C

| | | |
|---|---|---|
| Engine Oil Pressure | Engine Turbocharger Compressor Inlet Temperature | Right Front Tire Pressure, Corrected at 20c |
| Engine Oil Level | | Right Front Tire Pressure |
| Engine Oil Filter Differential Pressure | Engine Intake Manifold 4 Temperature | Left Rear Outside Tire Temperature |
| Engine Exhaust Gas Temperature | Engine Intake Manifold 3 Temperature | Left Rear Outside Tire Pressure Target |
| Engine Exhaust Gas Port 16 Temperature | Engine Intake Manifold 2 Temperature | Left Rear Outside Tire Pressure Minus Target |
| Engine Exhaust Gas Port 15 Temperature | Engine Intake Manifold 1 Temperature | Left Rear Outside Tire Pressure, Corrected at 20c |
| Engine Exhaust Gas Port 14 Temperature | Boost Pressure - Right Bank | Left Rear Outside Tire Pressure |
| Engine Exhaust Gas Port 13 Temperature | Boost Pressure - Left Bank | Left Rear Inside Tire Temperature |
| Engine Exhaust Gas Port 12 Temperature | System Voltage | Left Rear Inside Tire Pressure Target |
| Engine Exhaust Gas Port 11 Temperature | Right Rear Outside Tire Temperature | Left Rear Inside Tire Pressure Minus Target |
| Engine Exhaust Gas Port 10 Temperature | Right Rear Outside Tire Pressure Target | Left Rear Inside Tire Pressure, Corrected at 20c |
| Engine Exhaust Gas Port 9 Temperature | Right Rear Outside Tire Pressure Minus Target | Left Rear Inside Tire Pressure |
| Engine Exhaust Gas Port 8 Temperature | Right Rear Outside Tire Pressure, Corrected at 20c | Left Front Tire Temperature |
| Engine Exhaust Gas Port 7 Temperature | Right Rear Outside Tire Pressure | Left Front Tire Pressure Target |
| Engine Exhaust Gas Port 6 Temperature | Right Rear Inside Tire Temperature | Left Front Tire Pressure Minus Target |
| Engine Exhaust Gas Port 5 Temperature | Right Rear Inside Tire Pressure Target | Left Front Tire Pressure, Corrected at 20c |
| Engine Exhaust Gas Port 4 Temperature | Right Rear Inside Tire Pressure Minus Target | Left Front Tire Pressure |
| Engine Exhaust Gas Port 3 Temperature | Right Rear Inside Tire Pressure, Corrected at 20c | In Excessive Idle |
| Engine Exhaust Gas Port 2 Temperature | Right Rear Inside Tire Pressure | GPS Snapped Data Age |
| Engine Exhaust Gas Port 1 Temperature | Right Front Tire Temperature | Accelerometer Temperature |
| Engine Total Fuel Used | Right Front Tire Pressure Target | G-force Z-axis Peak |
| Engine Fuel Temperature | | G-force Z-axis RMS |
| Engine Fuel Rate | Right Front Tire Pressure Minus Target | G-force X-axis RMS |
| Service Hours | | G-force X-axis Peak-Peak |
| | | G-force Y-axis Peak |
| | | G-force X-axis Peak |
| | | G-force Y-axis RMS |

FIG. 7D

| | | |
|---|---|---|
| G-force Y-axis Peak-Peak | Front Aftercooler Temperature Coolant | Haul Distance |
| G-force Z-axis Peak-Peak | Engine Oil Level | Right Rear Minus Left Rear Suspension Cylinder |
| Brake Stroke | Engine Oil Pressure | TKPH R Warn |
| Brake Filter | Engine Oil Filter Differential Pressure | TKPH R Tires |
| Retarder3 | | TKPH F Warn |
| Retarder | Left Exhaust Temperature | TKPH F Tires |
| Parking Brake | Right Exhaust Temperature | GPS Snapped Point ID |
| Brake Air Pressure | | GPS Snapped Direction of Travel |
| Right Rear Brake Temperature | Right Minus Left Exhaust Temperature | GPS Snapped Incline |
| Left Rear Brake Temperature | Fueling Indicator | GPS Time of Equipment |
| | Fuel Filter Bypass | GPS Elevation of Equipment |
| Right Front Brake Temperature | Engine Fuel Consumption | |
| Left Front Brake Temperature | Engine Fuel Rate | GPS Snapped Latitude of Equipment |
| | Fuel Level | |
| Left Rear Minus Left Front Brake Temperature | Service Hours | GPS Latitude of Equipment |
| | Boost Pressure | |
| Right Front Minus Left Front Brake Temperature | Right Turbocharger Inlet Pressure | GPS Satellites Tracked |
| | | GPS Heading of Equipment |
| Right Rear Minus Left Rear Brake Temperature | Left Turbocharger Inlet Pressure | GPS Incline |
| Right Rear Minus Right Front Brake Temperature | Peak Air Filter Restriction | GPS Ground Speed of Equipment |
| | System Voltage | |
| User Shutdown | Auto Lube Status | GPS Fix Quality |
| Cold Mode Status | Payload Status | GPS Horizontal Dilution of Position |
| Engine Speed | Hoist Screen | |
| Engine Load | Body Lever | GPS Active |
| Throttle Position | Hoist Lever Position | GPS Snapped Point Confidence Level |
| Ambient Air Temperature | Body Position | |
| Atmospheric Pressure | Left Rear Suspension Cylinder | GPS Snapped Longitude of Equipment |
| Crankcase Air Pressure Gauge | Right Front Suspension Cylinder | GPS Longitude of Equipment |
| Engine Power Derate Percentage | Left Front Suspension Cylinder | Rotation Y-axis Peak |
| | | Rotation Y-axis RMS |
| Engine Coolant Level | Right Rear Suspension Cylinder | Rotation Z-axis RMS |
| Engine Coolant Flow | | Rotation Y-axis Peak-Peak |
| Engine Coolant Temperature | Payload | |
| Rear Aftercooler Temperature Coolant | Right Front Minus Left Front Suspension Cylinder | Rotation Z-axis Peak-Peak |
| | | Rotation X-axis RMS |

FIG. 7E

| Column 1 | Column 2 | Column 3 |
|---|---|---|
| Rotation X-axis Peak-Peak | Left Rear Inside Tire Pressure | Right Rear Outside Tire Pressure Minus Target |
| Rotation X-axis Peak | Right Rear Outside Tire Pressure Target | Right Front Tire Pressure Minus Target |
| Rotation Z-axis Peak | Left Front Tire Temperature | Left Front Tire Pressure Minus Target |
| Differential Oil Level | Left Rear Outside Tire Pressure | |
| Differential Filter Switch Bypass | Right Rear Inside Tire Pressure | |
| Differential Temperature Oil | Right Front Tire Temperature | |
| Differential Lube Pressure | Left Rear Inside Tire Temperature | |
| Torque Converter Screen | Right Front Tire Pressure | |
| Torque Converter Filter Bypass | Left Front Tire Pressure | |
| Torque Converter Outlet Temperature | Right Rear Outside Tire Pressure | |
| Lockup Slip | Right Rear Inside Tire Temperature | |
| Transmission Gear Numeric | Left Rear Outside Tire Temperature | |
| Transmission Lube Filter Bypass | Right Rear Outside Tire Temperature | |
| Transmission Charge Filter Bypass | Left Rear Inside Tire Pressure, Corrected at 20c | |
| Transmission Output Speed 1 | Left Rear Outside Tire Pressure, Corrected at 20c | |
| Transmission Lube Temperature | Right Rear Inside Tire Pressure, Corrected at 20c | |
| Ground Speed | Right Rear Outside Tire Pressure, Corrected at 20c | |
| Transmission Slip OHT | Right Front Tire Pressure, Corrected at 20c | |
| Transmission Gear | Left Front Tire Pressure, Corrected at 20c | |
| Gear Select By Operator | Left Rear Inside Tire Pressure Minus Target | |
| Low Steering Pressure | Left Rear Outside Tire Pressure Minus Target | |
| High Steering Pressure | Right Rear Inside Tire Pressure Minus Target | |
| Left Front Tire Pressure Target | | |
| Right Front Tire Pressure Target | | |
| Left Rear Inside Tire Pressure Target | | |
| Right Rear Inside Tire Pressure Target | | |
| Left Rear Outside Tire Pressure Target | | |

FIG. 7F

SYSTEM AND METHOD FOR DETERMINING A LOCATION OF ORE IN A STOCKPILE

FIELD

The disclosure relates to using mine operation data and leach analytics for training a predictive model, forecasting future operations and comparing to actual data, to adjust leaching operations and to optimize metals production.

BACKGROUND

Traditionally, ores have been routed to a particular processing system based on the mineralogy of the ore. For example, copper oxide and carbonate ores (e.g., cuprite, chrysocolla, malachite, and azurite) may be very amenable to leaching. Exposure to dilute sulfuric acid carries sufficient chemical energy to put the copper into solution, so that the copper can be purified and recovered by the downstream processing methods of solvent extraction and electrowinning. Leach recoveries from oxide and carbonate minerals can approach 100% of the contained copper, provided sufficient acid is available for leach reactions.

Acid cost should also be considered because it may not be economically possible to provide all the acid that the ore requires to release all of the contained copper. Gangue minerals (which are present in heap leach operations) consume acid but yield no value. The type and amount of gangue minerals determine the amount of acid that will be consumed, so mineralogical analysis and laboratory testing is used to determine whether an ore is economic to leach. If the cost of the acid for the process is greater than the value of copper obtained, the ore is not economic to process.

Advancements in leach technology have also made it possible to recover copper from secondary copper sulfides (e.g., chalcocite and covellite) via leaching. To break the copper-sulfur bonds in these minerals, oxidation is used. Sulfuric acid carries some oxidizing potential, but much of the driving force for leaching sulfides comes from the oxidation potential of ferric iron in solution. The presence of iron ions in solution is usually due to the leaching of iron bearing minerals present in the heap leach. When ferric iron oxidizes copper sulfide minerals, the ferric iron is converted to ferrous iron. The ferrous iron is converted back to ferric iron to further oxidize copper sulfide minerals. For this re-oxidation to occur, a source of oxygen or oxidation is used. The top and sides of a heap leach stockpile are open and atmospheric oxygen is readily available (so the heap surface area is a variable). However, within a heap leach (e.g., within a multi-lift heap leach structure), the interior may be oxygen starved and copper recovery may be adversely impacted. To help overcome this problem, various means of introducing oxygen into the interior of the heap leach structure may be used. Air or oxygen may either be introduced by physically piping or blowing it into the ore structure, by influencing the dissolved oxygen or oxygen potential of the leach solution, or by direct oxidation (which may be chemical oxidation). In heap bioleaching, oxidizing microorganisms (which may be naturally occurring) convert ferrous iron to ferric iron and thus aid the leaching operation.

In another class of minerals (e.g., the primary sulfides), copper is more tightly bound to iron and sulfur within the mineral lattice. An example of these minerals is chalcopyrite. Although much work is currently being performed to leach chalcopyrite bearing minerals, generally leach recovery from these minerals is low (e.g., around 15% of the contained copper). This usually results in these minerals being sent to froth flotation and smelting. However, some chalcopyrite may be placed on leach stockpiles, either because the chalcopyrite is mixed with other (more leachable) minerals or because the chalcopyrite is contained in ore whose copper grade was too low (below mill cutoff-grade) to be processed economically via the froth flotation and smelting route. The leach recovery from chalcopyrite minerals may be improved by using leach additives (of various types) to leach solutions or by adding the solutions directly to the ore.

Temperature is also a factor for leaching both secondary sulfides and primary sulfides. Temperature may increase recovery on the order of, for example, 0.5% for every 1 degree Celsius, provided sufficient oxygen is present for the oxidation reactions to proceed; however, such an increase in recovery may be impacted by several considerations, ranges and practical limits. While temperature may be increased by heating of air or leach solutions, the temperature may also increase due to the balance of exothermic chemical reactions and/or endothermic chemical reactions occurring within the leach stockpile (e.g., the oxidation of pyrite). Therefore, for any sulfide leach operation, the amount of pyrite present may be a variable.

Mineral mixtures and clays may contain copper in such a way that it is not economically recoverable by leaching. This copper is bound within complex mineral lattices and does not respond to acid or aeration. To calculate the maximum recoverable copper from a leach stockpile, it is helpful to know the amounts of these refractory copper minerals.

Assays that are available for specific volumes of ore are called blasthole assays because the assays are run on the ore which results from drilling blast holes into the ore. Available assays include TCu (the total percentage of copper in the sample), QLT (Quick Leach Test) which is a test that is an indicator of the presence of leachable minerals (e.g., sulfide) in the ore, and ASCu (Acid soluble copper) which is the amount of copper that is leachable by the application of acid alone. Another assay that is available is Ore Acid Consumption, which measures the amount of acid that a ton of ore will consume. If the acid consumption is too high, the cost of the acid may exceed the copper that could be recovered, such that the material may be uneconomic.

When it has been determined that the existing mineralogy is amenable to heap leaching, and other economic conditions are favorable, ore is placed on stockpiles in preparation for leaching. Optimization of ore placement may maximize the profit from a leach operation. Ores that have a high enough copper grade, favorable leach recovery and favorable days under leach (e.g., kinetics) may be crushed and agglomerated prior to conveyor stacking on a leach pad. In these circumstances, the amount of copper that is projected to be recovered via leaching from the ore is more than sufficient to cover the costs of haulage and crushing to a P80 size of less than about 1" (and often with a P80 of less than ¾" or ½"). The P80 size of an ore size distribution is a measure of particle size distribution having the screen size through which 80% of the particles may pass. The crushed ore may be conveyed into a large, rotating agglomeration drum, where the ore is mixed and wetted with at least one of (or a mixture of) water, reclaimed water, brine, raffinate, ILS (Intermediate Leach Solution), PLS (pregnant leach solution), sulfuric acid, another metal bearing product or products, an auxiliary oxidant, a halide salt, a binder, one or more additives to enhance galvanic leaching, or other leach additives. One purpose of agglomeration is to attach fine particles to coarser particles so that the particles do not migrate through the stockpile and ultimately cause the permeability of the structure to be decreased. Another purpose of agglomeration is to expose the ore to acid and lixiviants so that the leaching process is started. Yet another purpose of agglomeration is to create ore aggregates with optimum leaching characteristics.

After being agglomerated, the ore is fed onto mobile stacking conveyors and is deposited in a layer whose thickness (lift height) may be determined by the average leach characteristics of the ore being stacked (usually between 15-30 feet high). If the ore being stacked is a sulfide ore or has a sulfide component that would benefit from oxidation, air-lines may be installed in the ore (e.g. laid down under the ore that is to be stacked). These air-lines may be attached to a header which may protrude through the exposed side of the leach pad structure. These headers may be attached to large blowers that blow ambient air into the leach stockpile. The volume of air blown into the stockpile and the geometry of air-lines both influence the efficiency with which air can be introduced to the leach process. As the ore is stacked, an earthen structure is formed by the ore such that the top surface of the pad is relatively flat, while the sides (side slopes) of the pad are at the angle of repose of the damp ore.

After an area of the pad has been stacked with ore, an arrangement of leach lines (e.g., drip lines) may be placed on the top surface of the ore. Leach lines may also be placed on the side slopes of the leach pad structure so that the volume of ore around the sides of the pad is included in the leach operation. Leach solution (which may be a mixture of raffinate, ILS, PLS, water, sulfuric acid, an auxiliary oxidant, and a leach enhancing additive) is pumped through the leach lines and is dripped or sprayed onto the ore. The choice of using drip emitters or sprayers (e.g., wobblers) to introduce leach solution to the ore depends on such factors as the mineralogy of the ore. Sulfide ores have improved recovery when leach solution application rates are low, so drip emitters may be preferred. Sprayers may be used on oxide minerals, whose copper will leach by simply exposing the ore to acid. Plant water balance issues also influence the choice. If, due to weather events, too much water has entered the leach system, sprayers can be used to aid in evaporation.

An operational issue that may occur when drip emitters are used is plugging. Wobblers are not subject to plugging, so the wobblers may be used if leach solutions contain suspended solids that are not economical to remove. Because leach pads are very large, it is difficult to know whether leach lines are plugged. Plugged leach lines may be an operational issue because the ore under and adjacent to those leach lines will not be exposed to leach solutions and thus will not produce copper.

After the ore has been leached for a given number of days (days under leach or the leach cycle), the leach solution flow to the leach pad may be shut off and the pad may be allowed to partially dry out. The copper recovered after this first leach cycle is called first cycle recovery and represents most (about 80%) of the copper that may be recovered from that ore. At this point, the partially leached ore is either removed from the pad or prepared to be stacked over. In some leaching operations, leached ore is removed from the leach pad and restacked into a "ripios" stockpile in another location. This type of operation is called an "on/off pad" because the ore is put on the pad, leached, and then taken off. Unless the ripios are leached to recover residual copper, ores placed on an on/off pad will only achieve first-cycle recovery. In many leach operations, after ore has completed first cycle leaching, the older ore is left in place and fresh ore is stacked on top of the older ore. Air-lines may also be installed before the new ore is laid down. In these multiple lift heap leach operations, ore has multiple chances to leach, provided the driving forces for leaching are present in the lower lifts. These driving forces include sufficient acid so that free acid is present in the lower lifts, oxidizing potential exists (usually driven by the presence of ferric iron in solution), and sufficient permeability exists (so that leach solutions can contact mineral particles).

When ores do not contain enough recoverable copper to make crushing and agglomeration economic, the ore may be dumped by haul trucks onto leach dumps. The particle size distribution of this ROM (Run of Mine) ore is much larger than crushed ore with P80 sizes between 6 and 12 inches. Copper recoveries are lower for run of mine ores than crushed-leach ores because the percentage of the ore particles that are available for contact by leach solutions is lower.

The calculations which are used to determine the profitability of mining a particular section of ore depend not only on the properties of that ore (e.g., mineralogy, grade, leachability), but also on changing external factors of which leach operators and/or mine operators may have little control. Improved knowledge of expected leach recovery for each block of ore may allow mine operators to further optimize spending to maximize profitability. For example, the cost of blasting the ore in preparation for haulage is significant. This operation uses large drills which are used to create holes in the ore section at specific intervals. Each drill hole is loaded with explosive charges which are detonated to fragment the ore. Ore fragmentation is expensive, but it is one of the most efficient ways of size reduction in mining, as rocks generally have high compressive strength, but are more easily fractured by the tension and shear forces that are present in blasting. Blast fragmentation is an effective way of creating a finer particle size distribution, but the fragmentation comes at the cost of increased drilling and higher usage of explosive agents. This reduced particle size distribution can benefit leach recovery because it exposes a higher percentage of mineral particles, but it also produces more fine particles that could cause permeability problems during leaching. The benefits of blast fragmentation are more obvious for ROM ores which do not undergo further size reduction, but the benefits also translate to crush-for-leach ores because crushing energy is reduced.

Another variable cost is the diesel fuel used by large mining haul trucks, shovels and other equipment. The price of this commodity causes swings in the costs of mining, and consequently, in the revenue that can be generated from each designated volume of ore. After the ore has been blasted to fragment the ore, the ore is loaded by large mining shovels into diesel fueled haul trucks. The distance between loading and the ultimate destination of a truck load of ore is the haulage distance. The costs of ore haulage are proportional to distance, but also depend on factors such as mine topography and the percentage of the haul that is uphill. Ore haulage costs are a significant mining cost and also depend on the cost of tires, tire life, and truck maintenance costs.

Mining companies typically prefer to recover copper from ores via heap leach and hydrometallurgical methods because such methods often involve lower operating cost compared to processing the ores using, for example, froth flotation and smelting. Additionally, hydrometallurgical processes require less energy and water than traditional mineral processing operations. Accordingly, a strong need exists to develop a system that determines how to route ore to the most advantageous process by considering input data related to, for example, mineralogy data, irrigation data, raffinate data, heat data, lift height data, blower data, geographic data on ore placement, ore grade, recovery, processing cost and/or process efficiency. Furthermore, optimizing heap leach not only influences ore delivery logic, but also may optimize production and minimize operating inefficiencies and costs for mining (e.g., leaching) operations. The use of algorithms, automation and logic to drive decreases in operating costs and improved recovery of copper and by-product elements may lead to significant increases in ore reserves (i.e., more mineralized material becomes economic ore). Increases in ore reserves may lead to increased mine life and more accurate long-term mine operation decision making. The inputs and variables that may be used for ore routing and process optimization calculations are often changing, complex and interdependent. The potential predictive variables for leach production may include, for example, raffinate flow rate, raffinate chemistry, ambient temperature, ore temperature, days under leach, side slope irrigation, wobbler vs drip, TCu percentage (the total percentage of copper in the sample), QLT (Quick Leach Test) percentage which is a test that is an indicator of the presence of leachable minerals (e.g., sulfide) in the ore, P80 size, ore permeability, ore hardness, ore moly percentage and/or byproduct value percentage. P80 is often used to describe a particle size distribution, wherein the screen opening size is such that more than 80% of the particles would pass through. These variables may be highly correlated and not all of these variables may have predictive power in an individual predictive model. Further, these data come from a variety of sources and exist in a variety of electronic data formats.

A need exists to combine and utilize the input data in science-based subprograms (that feed outcomes to overarching algorithms) so that the true chemical and physical driving forces that impact leach recovery can be understood in a way that allows adjustments to interacting sets of parameters to drive beneficial change in mining (e.g., leaching) operations. Additionally, a need exists for checking output data against reality so that models can be adjusted for increasing accuracy and/or consistency. With such a system in place, ore routing calculations may change in real-time to adjust for changes in input variables. Additionally, heap leach efficiency (which impacts the ore routing model) may be optimized by influencing the chemical and physical forces that drive copper extraction. The powerful functionality that leach analytics provides goes beyond collecting data from various sources into one overarching database. Leach analytics provides a means for physically understanding how controllable variables impact leach recovery. Going further, leach analytics provides a means for quantifying complex variable interactions and their collective impact on leach recovery. Therefore, this complete analysis provides the basis of a control strategy such that variables may be changed to optimize an outcome. These changes may be tested manually and then incorporated into interacting automated control systems.

SUMMARY

In various embodiments, and as set forth in FIG. 5, the system may include a method comprising receiving, by a processor, historical data, wherein the historical data comprises at least one of mineralogy data, irrigation data, raffinate data, heat data, lift height data, geographic data on ore placement or blower data (step 505); training, by the processor, a predictive model using the historical data to create a trained predictive model (step 510); adding, by the processor, future assumption data to the trained predictive model (step 515); running, by the processor, the forecast engine for a plurality of parameters to obtain forecast data for a mining production target (step 520); comparing, by the processor, the forecast data for the mining production target to the actual data for the mining production target (step 525); determining, by the processor, deviations between the forecast data and the actual data, based on the comparing (step 530); and changing, by the processor, each of the plurality of parameters from the forecast data to the actual data to determine a contribution to the deviations for each of the plurality of parameters (step 535).

The method may also include overriding the receiving by inputting different historical data. The method may further include cleaning the historical data and/or removing the historical data that is bad data. The method may also include validating the predictive model using test data with a time lag. The method may also include running a simulation engine to replace one or more of the historical data with alternate data. The method may additionally include re-training the predictive model based on the deviations.

The historical data may be for a stockpile during a time period. The predictive model may be a Generalized Additive Model. The mineralogy data may include at least one of TCu percentage, XCu percentage (also known as ASCu or acid soluble copper), QLT percentage, ore size or tons. The irrigation data may include at least one of raffinate application rate, area under irrigation or days under leach (DUL). The raffinate data may include at least one of raffinate flow rate, raffinate $Cu^{2+}$, raffinate total iron (TFe), raffinate $Fe^{2+}/Fe^{3+}$, the types and quantities of leach modifying additives or catalysts, raffinate acid or cure acid. The irrigation data may include raffinate application rate comprising at least one of slide slope irrigation, wobbler v drip, ore permeability, ore hardness or ambient temperature.

The blower data may include ambient temperature, a temperature change when a blower is activated and a status of the blower as being activated. The temperature change may be derived from the exit temperature out of the blower detected by a sensor on the blower. The status of the blower as being activated may be determined from a temperature difference between the ambient temperature and an exit temperature from the blower is above a threshold. The heat data may estimate in-pile temperature and the heat data may include at least one of heat soft sensor data or measured temperature data (e.g., using a thermistor).

The historical data may further comprise at least one of PLS (pregnant leach solution) data, stockpile data or section mapping data. The stockpile and section mapping data may comprise at least one of Mine Material Tracking (MMT) tool data, Section Polygons (e.g., ArcGIS), elevations data, or Rules-based Matching data. The rules-based matching data may comprise at least one of dispatch data or haul truck sensor data (e.g., from any of the sensors in FIG. 7A-7F) for loading and dumping. The MMT tool data may comprise at least one of load point data, shovel high precision GPS data, terrain data, haul truck sensor data, mine system data, block model data and dispatch data. The block model data may comprise transformed 3D assay data from 3D interpolation of an assay from a drill hole. The historical data may further comprise ore map data.

The ore map may leverage predictions from a column test predictive model, which may be trained on large scale laboratory tests. The ore map data may include truck dump data. Column tests may include large scale laboratory tests performed on a given quantity of ore which may be loaded into a vertical column and leached to simulate or optimize field conditions. A machine learning model (e.g., multi-layer perceptron (MLP)) may receive data from the column test to create the column test predictive model. The machine learning model may also receive and use bio data (e.g., additives, microbes, or catalysts). The column test may provide output data including at least one of days under leach of a mineral, the percentage of each mineral reacted or amount of acid consumed. The column test input data may include at least one of raffinate TFe, raffinate acid, leach additive or catalyst, raffinate $Cu^{2+}$, days under leach, XCu, QLT, application rate or cure acid. The irrigation data may comprise an area on calculation that determines a share of an area of the stockpile that is being irrigated. The ore map may comprise section mapping data that includes creating a polygon map. The polygon map may include correcting for overlapping polygons. The polygon map may include creating shapes of an overlap portion of polygons with known ore characteristics. The future assumption data may include mine plan data. The mining production may include mining production from side slope leaching. The geographic data on ore placement may include the geographic location where the ore is placed in the stockpile.

In various embodiments, the system may further include a heat soft sensor method for determining a temperature profile of a stockpile comprising receiving, by a processor, adjustments to process parameters; determining, by the processor, a heat profile of a stockpile, based on the adjustments; determining, by the processor, the heat profile of the stockpile at different depths of the stockpile, based on the adjustments; and determining, by the processor, changes to the heat profile of the stockpile during a timeframe.

The determining of the heat profile of the stockpile may comprise estimating the heat transfer at a surface of the stockpile; estimating the heat transfer within the stockpile; and estimating the heat generation within an interior of the stockpile. The estimation of the heat transfer at the surface of the stockpile may be based on at least one of evaporation, convection, shortwave radiation exchange or longwave radiation exchange. The estimation of the heat transfer within the stockpile may be based on advection of raffinate moving down through the stockpile and advection of air within the stockpile. The estimation of the heat generation within the interior of the stockpile is based on at least one of exothermic chemical reactions or endothermic chemical reactions. The estimation of the heat generation within the interior of the stockpile may be based on oxidation of pyrite and sulfide ores. The system may modify the process parameters based on trend data of the heat profile. The heat profile of the stockpile may comprise section-level estimates of the heat profile.

The process parameters may comprise at least one of type of thermal film, the timeframe, depth of a lift in the stockpile, raffinate application flowrate on a surface of the stockpile, raffinate temperature, air application rate, air wet bulb temperature, rate of the evaporation of raffinate, shortwave infrared radiation absorptivity, longwave infrared radiation absorbed at the surface of the stockpile, longwave radiation emitted from the surface of the stockpile, exothermic heat generation within the stockpile, heat transfer by convection at a surface of the stockpile and/or average temperature at an end of the timeframe. The film may include any clear film, colored film or coated film. The film may include a layer of insulating material which may be ore, crushed rock or another crushed substance. For example, the type of film may include Mantos thermal film. The raffinate application flowrate may comprise a flowrate per unit area of the raffinate on the surface of the stockpile. The raffinate temperature may be used for overall heat balance. The air application rate may comprise a flow rate of air being injected per unit area and measured at a base of a newest lift in the stockpile, wherein the air travels up through the stockpile and exits from the surface and/or side slope. The air wet bulb temperature may be based on the air injected into the stockpile as it tends toward 100% humidity within the stockpile. The evaporation percentage may be based on a percentage of raffinate flow rate going in at the surface of the stockpile or as an independent evaporation rate. The shortwave infrared radiation absorptivity and emissivity may be based on incoming solar radiation that is reflected out and absorbed at the surface of the stockpile. The exotherm heat generation may be based on rate of energy produced as a result of the oxidation of ores and minerals within the stockpile. The heat transfer by convection at the surface of the stockpile may be based on at least one of heat loss directly to the air or heat loss through a thermal film cover.

In various embodiments, the system may include a method of mine material tracking comprising receiving, by a processor, data, wherein the data comprises load point data, shovel high-precision global positioning system (HPGPS) data, terrain data, provision data, haul truck sensor data (e.g., from any of the sensors in FIGS. 7A-7F), mine data (e.g., MineSight data), block model data and dispatch data; receiving, by the processor, chemical data and mineralogical data of ore at a plurality of blast holes; interpolating, by the processor, the plurality of blast holes in the block model data; assigning, by the processor, the plurality of blast holes to a geographic location post-blast; merging, by the processor, the geographic location post-blast, the dispatch data, the terrain data and the haul truck sensor data with the block model data; linking, by the processor, the block model data to a truck load based on the merging; aggregating, by the processor, ore characteristics for the truck load; capturing, by the processor, images of ore that is placed in the truck load to determine particle size distribution information about the ore; and determining, by the processor, a location of the ore in a stockpile.

The load point data may include HPGPS load points. The load point data may include at least one of terrain data, provision data or dig point data. The mine system data may include at least one of mine planning data or the block model data. The dispatch data may include at least one of haulage cycle data or beacon data. The haul truck sensor data may provide information about the haul trucks, as provided by any of the sensors in FIGS. 7A-7F.

In various embodiments, the system may include a method comprising receiving, by a processor, ore placement data for a stockpile, wherein the ore placement data may include dispatch data, haul truck sensor data (e.g., from one or more of the sensors in FIGS. 7A-7F), polygon data (e.g., GIS), assay data and mineralogy data; determining, by the processor, ore placement locations for the stockpile, based on the ore placement data; determining, by the processor, an amount of mineral extracted from the stockpile, based on historical leaching process data for the stockpile; and determining, by the processor, recovery locations for recoverable amounts of mineral in the stockpile, based on historical leaching process data for the stockpile.

The mineralogy data may be from the block model and included in the mine material tracking data. The ore placement data may include the estimated material extracted from the stockpile and may include data from a column test predictive model. Determining the ore placement locations of recoverable copper for the stockpile may include determining the total mineralogy for the stockpile. Determining the amount of mineral extracted from the stockpile may include determining a primary ore map for the stockpile. Determining the primary ore map for the stockpile may include adding flow data, irrigation data and a remaining mineral prediction from a supervised machine learning model estimating recovery in laboratory column tests (e.g., an MLP model) to obtain information by section and by date for the stockpile.

Determining the total mineralogy for the stockpile may include aggregating mineralogy details to a section level by combining MMT truckload data at a dump level, MMT imputation data at the dump level and MMT final section mapping data at the dump level and the section level; obtaining maximum days under leach (DUL) for each section at the section level by using irrigation data over all stockpiles at the section level; and determining an intermediate ore map for a stockpile by combining the aggregating mineralogy details, the maximum DUL for each section and a primary new section polygon.

Determining the primary ore map for the stockpile may include merging on the date and the stockpile at the date level and section level by combining the PLS, raffinate flow and/or chemistry (e.g., acid) concentration at the date level and the stockpile level with the irrigation on the stockpile at the date level and the section level; merging on the section at the date level and the section level by combining the merge on data and the stockpile with the intermediate ore map for the stockpile; predicting mineral recovery using a column test model with machine learning model predictions, based on the merge on section; and creating the primary ore map for the stockpile at the section level based on the estimated mineral recovery.

The reallocation of the ore in the neighboring sections to the side slopes of the stockpile may include merging on the date and the stockpile at the date level and section level; combining the raffinate flow and acid content at the date level and the stockpile level with the irrigation on the stockpile with acid content at the date level and the section level; combining the primary ore map for the stockpile at the section level with the primary new section polygon; combining the reallocating of the ore with the merge on data and stockpile to create the merge on section at the date level and the section level; predicting the mineral recovery using a column test model with machine learning model predictions, based on the creating the merge on section; and creating the primary ore map slope for the stockpile at the section level based on the mineral recovery.

The method may further include reallocating the ore in neighboring sections to side slopes of the stockpile. The method may further include providing a visualization of the recovery locations for the recoverable amounts of mineral in the stockpile. The method may further include determining at least one of x,y,z coordinates or time-series layering information for the recovery locations for the recoverable amounts of mineral in the stockpile. The method may further include providing a visualization of section mineralogy populated on a map of each of the stockpiles. The method may further include filtering of the sections by at least one of lift, stockpile or mineralogy composition. The method may further include displaying aggregated values for at least a subset of the sections. The method may further include defining boundaries of the stockpiles and the sections based on polygons recorded in a geographic information system (GIS). The method may further include mapping dump locations of haul trucks into the polygons based on combined signals from at least one of MMT location information, GPS coordinates or a map of section identifiers and sub-piles to the stockpiles. The method may further include aggregating and averaging the MMT location information to estimate section-level characterizations of mineralogy and P80. The method may further include estimating the recoverable amounts of mineral in the stockpile based on a column test model. The method may further include calculating the recoverable amounts of mineral at the section-level by deducting estimated recovered mineral from initial placements. The method may further include determining which sections are economically viable for recovery via irrigation (which may include irrigation by drip, wobbler, or targeted injection of raffinate or raffinate enhanced with acid, additives, or oxygen) based on a number of contiguous high-remaining sections and the proximity of the high-remaining sections to a top lift.

In various embodiments, the system may include a method comprising: determining, by a processor, that a haul truck completed a dump; determining, by the processor, that a sensor on the haul truck is not accurate; determining, by the processor, that a location provided by a dispatch system is not accurate; and assigning, by the processor, the dump of the haul truck to a dummy location.

The determination that the haul truck completed the dump may include at least one of determining, by a processor, that a speed of a haul truck is below a threshold; determining, by the processor, that a gear of the haul truck is in park; determining, by the processor, that an emergency brake of the haul truck is set; or determining, by the processor, that a bed position of the haul truck passed a threshold height. The determining that the haul truck completed the dump may include receiving data from a beacon of a dispatch system about a time the haul truck arrived at a location and dumped a load. The determining that the haul truck completed the dump is based on data from a soft sensor that processes several measurements together using control theory. The determining that the sensor on the haul truck is not accurate is based on at least one of determining, by the processor, that the sensor is broken; determining, by the processor, that the sensor is not located on the haul truck; or determining, by the processor, that a location provided by a dispatch system is more accurate.

In various embodiments, the system may include a method comprising obtaining, by a processor, days under leach, chemistry data and mineralogy data from a column test of a column of ore from a section of a stockpile; adjusting, by the processor, process parameters applied to the column of ore to create controlled conditions; increasing, by the processor, accuracy of the chemistry data and the mineralogy data based on the controlled conditions; providing, by the processor, the chemistry data and the mineralogy data to a machine learning model to build a column test predictive model; and determining, by the processor using the machine learning model, estimated remaining mineral in the section of the stockpile based on the column test predictive model.

The chemistry data may be stored in a laboratory information management system (LIMS). The column test may simulate leaching in a section of ore in controlled conditions. The machine learning model may be a multi-layer perceptron (MLP). The chemistry data and the mineralogy data may include at least one of raffinate TFe, $Fe^{2+}$ feature, raffinate acid, raffinate additive, raffinate temperature, raffinate $Cu^{2+}$, XCu, QLT, application rate or cure acid (e.g., ORP, $Fe^{3+}$, etc). The machine learning model may further use agglomeration solution chemistry (e.g., acid concentration or agglomeration additive concentration) applied in the column test associated with mine for leach (MFL) processes.

The method may further include determining, by the processor using the machine learning model, the location of the estimated remaining mineral in the section of the stockpile. The method may further comprise adjusting agglomeration acid concentration applied in the column test associated with mine for leach (MFL) processes. The method may further comprise adjusting a mine plan based on the estimated remaining mineral. The method may further comprise transmitting the estimated remaining mineral in the section of the stockpile to an ore map. The method may further comprise training the column test predictive model on laboratory records of column test performance. The method may further comprise generating a mineral recovery prediction from the machine learning model. The method may further comprise generating, by the processor using the mineral recovery prediction, a mineral recovery curve to estimate mineral recovery from leaching over a period of time.

In various embodiments, the system may include a method comprising receiving, by a processor, location coordinates of vehicles making dumps on a second lift of a stockpile; aggregating and averaging, by the processor, the location coordinates of the vehicles to determine a location of the vehicles; receiving, by the processor, elevation data of the vehicles from the location coordinates of the vehicles; determining, by the processor, a second elevation of the second lift based on the elevation data of the vehicles; and determining, by the processor, a height of the second lift by deducting a first elevation of a first lift from the second elevation of the second lift. While the disclosure may include the phrase "second lift", the disclosure contemplates that the second lift may include any lift or subsequent lift. The second lift may be any lift that is higher than the first lift. For example, the second lift may be the tenth lift. Moreover, the phrases first lift and second lift may be used interchangeably.

The location coordinates of the vehicles may be determined at a time preceding the dumps. The location coordinates may be determined by a GPS sensor on each of the vehicles. The method may further comprise revising the height of the second lift by replacing the height with the conveyor height for crush-for-leach stockpiles. The method may further comprise determining an estimate of a boundary of the second lift based on paths that the vehicles traversed. In various embodiments, the system may revise the boundary elevation over time using sensors that measure points on the surface or interior of the stockpile.

In various embodiments, the system may include a method comprising receiving, by a processor, location coordinates of a vehicles making dumps on a second lift of a stockpile; aggregating and averaging, by the processor, the location coordinates of the vehicles to determine a location of the vehicle; and determining, by the processor, a dump location by comparing the location of the vehicles with GIS polygons and dispatch data.

An accuracy of the dump location may be increased by compensating for a periodic overlap in the GIS polygons. An accuracy of the dump location may be increased by compensating for the dispatch data recording a different beacon dump location. An accuracy of the dump location may be increased by compensating for entry errors about the dump location.

BRIEF DESCRIPTION OF THE DRAWINGS

A more complete understanding of the present disclosure may be derived by referring to the detailed description and claims when considered in connection with the Figures, wherein like reference numbers refer to similar elements throughout the Figures, and:

FIGS. 2A and 2B are a chart showing the features and data used by the system, along with descriptions, data sources and relationships with target variables, in accordance with various embodiments.

FIGS. 7A-7F include is a list of exemplary sensors that may acquire data for the system, in accordance with various embodiments.

DETAILED DESCRIPTION

Figure 1:
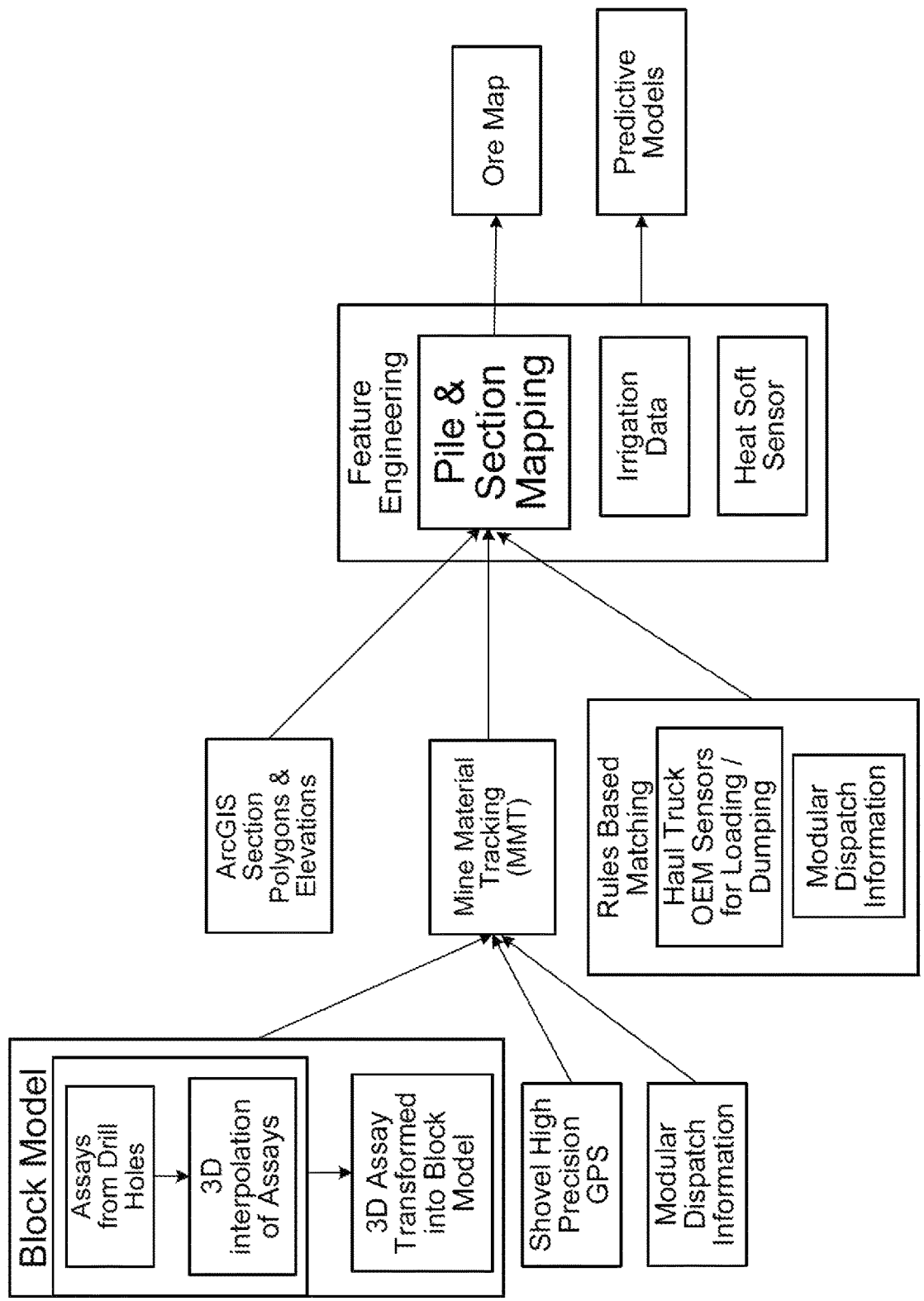
FIG. 1 is a flow chart showing the integration of the block model, MMT, and haul truck sensors, in accordance with various embodiments.

In general, the disclosure provides a system for better understanding and controlling the chemical and physical driving forces that impact leach recovery. In various embodiments, the system may include input data that is received by subprograms (predictive/recovery models) that provide outcomes that are used in algorithms (forecast engines). The system may disclose relationships between metallurgist decisions, operational conditions and mining production (e.g., copper production).

The software elements of the system may be implemented with any programming language or scripting language. While the system may be described in terms of copper production, the system may be similarly applicable to any type of minerals in any of the embodiments discussed herein. For example, the system may operate with any mineral for which value (e.g., metal value) may be recovered by leaching. While the system may be described with respect to haul trucks, shovels or other mining equipment, the system may operate and gather data from any type of vehicle or equipment in any of the embodiments discussed herein. While the system may be described in terms of raffinate or raffinate application, the raffinate may include other additives in any of the embodiments discussed herein. Moreover, the system may apply to acid or acid application since the acid may be part of the raffinate. In other words, the terms raffinate and acid may be used interchangeably in this disclosure.

The system may provide output data that may allow adjustments to interacting sets of parameters to drive beneficial changes in mining (e.g., leaching) operations. The input data may relate to, for example, ore grade, recovery, processing cost, process efficiency, mine plan, block models and/or ore map. The system may also adjust models for increasing accuracy and/or consistency by checking the output data against reality. The system may also change (e.g., in real-time) ore routing calculations to adjust for changes in the output variables. Additionally, the system may optimize heap leach efficiency (which impacts the ore routing decision) by adjusting and optimizing the chemical and physical forces that drive copper extraction. The system may provide high prediction power (about 8-16% error).

In various embodiments, the system may quantify the impact of using different parameters of chemistry, temperature, material size and duration on leaching production for a specific leach pad. In various embodiments, the system may consider truck load, mineralogy, irrigation, section history and PLS to create a digital twin model of the actual leach pad. The twin model of the actual leach pad may be used to simulate, forecast, backcast and ore map the optimal solution for copper recovery. In various embodiments, the system may create a virtual leach pad that may be used to simulate or forecast optimal conditions for recovery.

In various embodiments, the system may provide for leach pad optimization including placements and/or processing. The system may use ore placement targeting via dispatch, truck sensors (e.g., from one or more of the sensors in FIGS. 7A-7F), geographic information system (GIS) polygons and mineralogy from block model optimization to make better decisions about where to place ore and how to process the ore to improve production and/or recovery, while also considering real-world constraints. Machine learning models (e.g., predictive models) may be used to understand how ore characteristics and leaching practices impact both production and recovery at each stockpile. While the phrase predictive model may be used herein, the system contemplates the use of any machine learning model or supervised machine learning model. The leach pad optimization tool may build on these models to identify the best possible decisions to maximize stockpile production and/or recovery. To provide more practical recommendations, the system may implement constraints to reflect real-world limitations. The leach pad optimization tool may account for mineralogy information from the block model, dispatch and truck sensors, polygons, and the predictive models to create recommendations for where ore should be placed and how to leach it. Constraints may include, for example, available area, flow, acid, relative costs of transporting, relative costs of leaching and expected ore volume (produced by the mine and requiring placement). The leach pad optimization tool may consider thousands of data points (e.g., in seconds) to create practical recommendations (not replicable by humans) for maximizing production and recovery.

In various embodiments, the system may generally include a simulator, a machine learning model (e.g., predictive model), a forecast engine, a backcast engine and an ore map. In various embodiments, one model may cover multiple stockpiles. In various embodiments, a global model may summarize a leach at a phenomenological level that applies to any leach pile. In various embodiments, each stockpile or leach pad may be covered by a separate model. The term "stockpile" may be used herein, but the system may similarly apply to a stockpile, multiple stockpiles, a leach pad, multiple leach pads, a lift, multiple lifts, a section, multiple sections, etc. and the terms may be used interchangeably. The stockpile may include different layers called lifts (e.g., 50-foot height sections). A lift may be divided into sections, wherein the section may be any shape and size. Each section may be separately irrigated and tracked. The tracking for each section may include days under leach, raffinate flow, temperature monitoring, etc. The middle of a lift may include more uniform rectangular sections, while the edges of the stockpile may include irregular shaped sections because the edges may not be as uniform or consistently shaped as the middle of the lift. The system may also disclose herein the operation of a copper mine and the extraction of copper. However, similar systems, components, data and/or models may be used to obtain data about any type of mine or how to improve the extraction of any type of mineral.

In various embodiments, the system may incorporate data from different sources into the predictive model, ore map and/or forecast engine. The system may include data from various sensors throughout the mine. The sensors may be located at different areas of the chemical plants or stockpiles. Flow sensors may be used to determine the flow rate in certain pipes, which may be used to determine application rates. Oxygen sensors may be used to measure the oxygen content in the stockpiles. Solution collection devices may catch the leaching solution partway through its leaching process for analysis. Solvent extraction and electrowinning (SXEW) sensors may be involved with the setting and simultaneous purification of the post-leaching solution. The purified solution may then undergo copper electrolysis, which results in cathode copper that meets quality and quantity criteria. In various embodiments, the system may also acquire data from sensors such as, for example, piezometers, gaseous oxygen sensors, other gas sensors (e.g., CO, $CO_2$, $H_2S$, $SO_2$, NOx, and the like), dissolved oxygen sensors, flow meters, conductivity meters, resistivity meters, x-ray analytical equipment, pH sensors, ORP sensors, thermistors, temperature sensors, load sensors, and/or bioactivity sensors.

With reference to FIG. 1, certain inputs may include data from a block model. Assays from drill holes may be fed into a tool for 3D interpolation of assays. The 3D assay may be incorporated into a block model. The block model data, the shovel high precision GPS data and modular dispatch data may be inputs into the MMT (mine mineral tracking) Tool. The Rules-based Matching may receive inputs from one or more of the haul truck sensors for loading/dumping (e.g., as set forth in FIGS. 7A-7F) and dispatch data. The data from the MMT tool, the ArcGIS section polygons, elevation data, and the rules-based matching may be inputs into the stockpile and section mapping. The stockpile and section mapping, the irrigation data and the heat soft sensor may be part of the feature engineering tools that are fed into the predictive models. The stockpile and section mapping may be fed into the ore map. The system may receive other inputs from features or data, as set forth in FIGS. 2A and 2B, and as further described below. As set forth in FIGS. 2A and 2B, a "report" may provide a summary of what happened at the mine over a certain period of time (e.g., 24 hours, a shift, etc.). The report may include information about ore placement, chemical applications, content information, etc. The system may obtain certain information and data from the report to feed into the models. The report information may be obtained from inputted data, sensors, servers, databases, historical data, dispatch data, other systems, etc. The report information may include information from servers because the different sensors may communicate with servers (e.g., PI servers from OSI) such that the servers store all (or a subset of) the sensor data.

The servers and components may provide information to an enterprise server or database. The system may include a data engineering (DE) pipeline that ingests the raw data, builds out features, aggregates data, builds the dataset for the models, creates output shapes and/or provides output. The DE pipeline may include SQL queries, feature engineering in any suitable code (e.g., Python code), etc. The DE pipeline may generate model input tables for a feature store. The feature store may include a data cloud or warehouse (e.g., Snowflake data cloud) where the data is written out from the DE pipeline or a database (e.g., Cosmos database)

that stores different models and results (forecasts, backcasts, etc). The feature store may provide data for model training, etc.

The system may use the forecasts and predictions to implement operational changes to optimize copper recovery, in advance of the ore being placed. As such, the system may provide advanced notice for implementing changes in ore processing methods and commodities purchases. For example, if the model shows that increased blast fragmentation may help the mining process and be economic, the system may provide a notification (or send a signal to implement a change in the drilling system and the purchasing system) to modify blasthole drill spacing and purchase additional blasting material. If the model shows that adding more acid may help the mining process and be more economic, the system may provide a notification (or send a signal to implement a change in the purchasing system) to purchase more acid at an advantageous price. If the model shows that copper extraction would be improved by higher temperature leaching, the system may provide a notification that the ore should be routed to a stockpile where heap covers or heat addition systems may be employed. Heat addition systems may include the use of solar, geothermal and/or heat from other processing operations by use of heat pumps, heat exchangers and/or direct heating technologies. Moreover, if the model shows that copper extraction would be improved by higher temperature leaching and/or aeration, the system may provide a notification or signal to air blowers (or an operator of the air blowers) to automatically increase airflow and increase the pile temperature. Further, ores that benefit from leaching at higher temperatures may (as shown by the heat soft model) benefit from co-placement with materials containing elevated levels of pyrite (generally above 2%). The system could provide notification to mine planners or input to mine planning models, so that pyritic materials are most beneficially co-placed with ores to increase leach temperatures through exothermic reaction mechanisms. In yet another example, sulfide ores which may benefit from air injection may be routed (based on a notification or instruction form the system) to stockpiles where air injection equipment (blowers and ducting) are located. In another example, for ores which may benefit from exposure to one or more leach additives or combinations of additives, the system could provide a notification (or send instructions to implement the change at an additive distribution machine), so that the optimum combination of additives is provided to the ore at the correct point in the leach cycle. Additionally, the model may show that a specific combination of parameters may provide optimized metal value recovery. In this case, the system may provide a notification (or send instructions) to make process changes such that each unit of ore mined is processed under optimized conditions. In various embodiments, the system may send a signal to other systems to change irrigation rates and/or aeration rates, in response to measured (e.g., real-time measurements), estimated and/or calculated inputs to the optimization simulations (e.g., optimization algorithms in a module). For example, if the system shows that a stockpile exhibits higher copper recovery when raffinate iron contents are high, the system may provide notification or send a signal to an iron addition system so that iron ions are added to the raffinate. The iron ions may be added to the raffinate by the addition of new iron to the system by a chemical addition system or by re-routing high iron solutions from other stockpiles. In another example, if the model shows that the biological content of a leach solution is beneficial for copper recovery, the system may provide a notification or send a signal to a bio-plant so that additional beneficial microbes are added to leach solutions. In another example, if the model determines that copper extraction is improved when raffinate copper concentrations are low, the system may provide a notification or send signals so that copper extraction in downstream solvent extraction plants is increased, thus providing a low grade raffinate.

The system may expedite the process of providing the feedback and forecasts. Prior to using the model, the feedback may have suggested that the stockpile variables were outside an appropriate range, so an expert would be needed to be scheduled, the expert would need to come onsite to analyze the stockpile variables, then the expert would need to draft a report about the findings. However, expert reviews take time. In one instance, the day the expert report was obtained confirming the stockpile variables were outside an appropriate range, the stockpile blew out. With the model, the system may suggest (within hours) changes to implement to cause the variables to be in an appropriate range.

In various embodiments, the system may include piezometers (or pore pressure meters) that allow the measurement of the magnitude and distribution of pore pressure and the variation of pore pressure throughout the life of the leach stockpile. The data from an array of piezometers can be used to evaluate flow patterns within the stockpile and the effectiveness of any control measures. In addition to addressing safety concerns with heap stability, data from piezometers could inform the system when leach solutions are channeling within the stockpile and therefore not contacting ore particles uniformly. The system may use such information to identify the potential for unleached copper in a given area so that the unleached copper could be designated for recovery via methods such as, for example, re-mining or deep raffinate injection.

The forecast may be used to optimize future mine plans. Based on the forecast, the optimization process may be applied to inputs to suggest impactful changes. The system may suggest DUL (days under leach) cycles based on optimal forecasted production. The system may provide cross-pile forecasts that may drive optimization of placements between leach stockpiles. The system may determine an optimal diversion of raffinate between stockpiles to maximize leach production, so the system may send a signal to the raffinate dispenser or router to divert the raffinate over a different pathway. The system may determine dump allocations to lifts/piles based on forecasted production, so the system may send signals to the routing system (or directly to automated haul trucks) to change the routing of the haul trucks. The ore map tool may determine areas to automatically re-leach based on remaining Cu calculations, so the system may send a signal to a dispenser to automatically start a re-leaching process. The ore map may also determine areas to be re-mined based on a determination that re-mining efficiencies may exist, so the system may send a signal to a scheduling system or mining machine to start re-mining a certain area. In various embodiments, the system may determine that a particular stockpile on a particular area of a stockpile may benefit from increased acid addition. As such, the system may send a signal to an auto-valve that could be directed to open to a setpoint so that additional acid is added to the raffinate destined for a particular area under leach or to be leached. In various embodiments, the system may also determine (based on previous data or a column test model) that ore placed in a particular area of a stockpile may benefit from the addition of an additive or a combination of additives, microbes, and leach catalysts. As such, the system may send a signal to one or more auto-valves that could be directed to open to setpoints, so that one or a combination of additives, microbes, and leach catalysts may be added to the raffinate bound for a given area of the leach stockpile. Being able to model leach optimizations for future ore placements is also beneficial in that mine and haulage plans may be adjusted in advance. For example, if the system determines that ore from one or more locations in the mine would provide optimal copper recovery if it were stacked at a certain lift height (e.g., 20 feet), the mine plan can take this into account. An accumulation of data on optimal lift heights for all the ore to be leached year by year may allow calculations of stockpile dimensions to meet production requirements. These calculations may further help with enhanced land planning and water planning.

Figure 3:
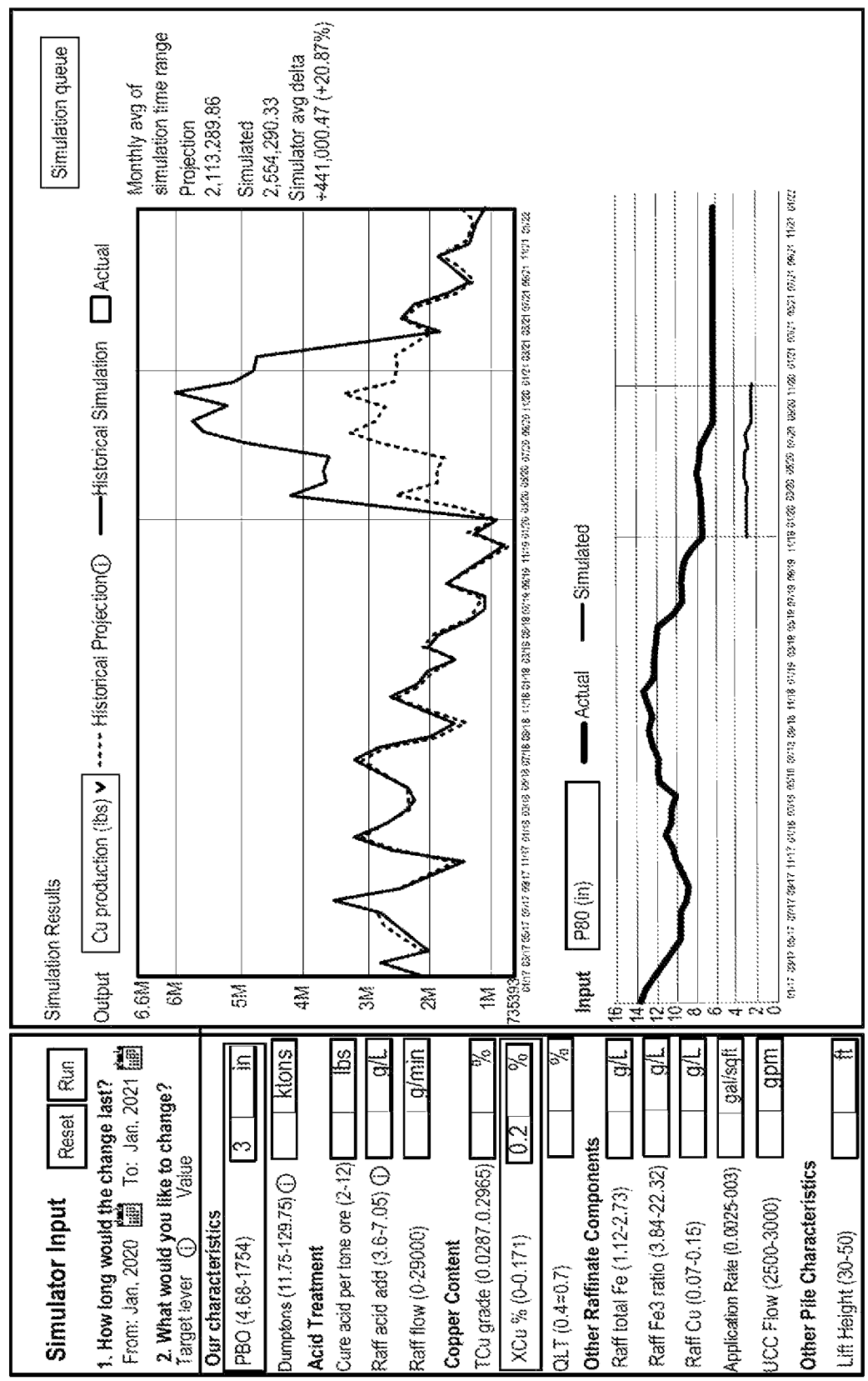
FIG. 3 is a screen shot of simulator input and simulation results, in accordance with various embodiments.

The simulator may be part of (or interact with) the predictive model because the simulator may adjust the historical data in the predictive model (wherein the predictive model was trained with such historical data). As shown in FIG. 3, in various embodiments, the simulator may run experiments to find production-maximizing recipes across different process parameters. The simulator may leverage the predictive model to run "what if" scenarios by replacing observed historical values with user-set or automatically determined alternate values. The model may be trained on the distribution of data, and the model may be re-run with the alternative value. The alternative values may not be a direct change to a process parameter; rather, the alternate value may include a change to an average value during the simulated time period. For example, the simulator may provide what the production should have been if P80 had been an inch smaller on average for the last year. The simulator provides the alternative values or changed values to the predictive model, and the system re-runs the prediction model with the alternative values or changed values to provide a simulated result. For example, the simulator may provide the production value of a particular stockpile if the acid dosage had been increased or decreased. Further, the simulator may provide the impact of placing ore of a given mineralogy on the leach stockpile. If, for example, an ore having high acid consumption was placed on the stockpile, the simulator may provide an estimate of the impact of other ore within the stockpile being acid starved during leaching. In another example, the simulator may provide the production value of a particular stockpile if the temperature during leaching had been increased. The simulator may adjust other variables such as, for example, raffinate flow, mineralogy, ore information, life height and cure acid per ton. The raffinate flow may include, for example, raffinate flow plus separate UCC raffinate flow option for a stockpile, application rate, raffinate acid, raffinate TFe, raffinate Fe ratio, and/or raffinate $Cu^{2+}$. Mineralogy and ore information may include TCu grade, XCu grade, QLT, P80 and/or dumptons.

The system may include a platform for receiving and combining the inputs. The inputs may be considered x values. The system may use, for example, a predictive model for combining all or any subset of the various inputs. In various embodiments, the predictive model may include a GAM (Generalized Additive Model). A GAM is a linear model that may also model nonlinear data. A GAM may not be restricted to a relationship that is a simple weighted sum, but instead, the GAM may assume that the outcome may be modelled by a sum of arbitrary functions of each feature. The GAM may replace beta coefficients from linear regression with a flexible function which allows nonlinear relationships. This flexible function may include a spline. A spline may include complex functions that allow the modeling of non-linear relationships for each feature. The sum of many splines may form the GAM. The result is a highly flexible predictive model which still may be partially explained with a linear regression. The complexity of the GAM may be controlled in accordance with domain expertise. The system may define the shape of each input relationship and the GAM model may learn the shapes for each of the many inputs. The GAM model may combine the input relationships to create an overall prediction. The system may evaluate the GAM model performance using, for example, $R^2$ (percent variance explained) and MAPE (percent error/accuracy).

In various embodiments, the predictive model may use historical data to create a prediction about the expected direct production in the stockpile or leach pad based on how the stockpile or pad was managed. The system may build a mathematical representation of the stockpile (e.g., using geologic data and mineralogic data). The system may obtain data about the stockpile based on any time period (e.g., each day). The predictive model may also use similar data that helps to generate the ore map.

In various embodiments, the predictive model may be trained by combining such historical data values in such a way that results in an outcome. The outcome of the predictive model may be considered a y-value. The predictive model may, for example, analyze onsite leaching initiatives and estimate the value of potential interventions. For example, the predictive model may help determine what the effect of decreasing P80 by 1 inch in a stockpile will be in Q4 of 2022. In another example, the predictive model may determine what the effect of increasing or decreasing the acid content of the raffinate will be in Q1 of 2023. After the predictive model uses the training set of data, the system may validate the predictive model. The trained predictive model may be provided with a test set of data to validate the model. The test set of data may include data that is different from the training set of data. When obtaining the validation data, in various embodiments, the system may split the data and/or incorporate a time lag with a rolling time window (out-of-time validation or walk forward validation). One of the reasons for the lag is that the quantity of the new ore may be insignificant compared to the very large stockpile. As such, the new ore placed on a large stockpile may not impact the stockpile production for weeks or months, so system uses the historical data from a previous time period. The system does not use training data from the day that the system is trying to predict for, but rather uses historical training data from weeks or months prior to the day the system is trying to predict for. For example, the system may use training data from January-March, but the test data may be data from May-June (skipping April data). The test set of data may include the x values (inputs), then the predictive model may calculate the y value (output). As such, the validation process may use the test data to help determine if the training data set has one or more flaws.

The system may provide for enterprise aggregation of leach data that includes the synchronization of the leach data across business units and/or across mines. The system may create or adjust the predictive model based on new predictive abilities due to analytics. The predictive model may be based on empirical data, and not physical or chemical equations.

In various embodiments, the system may also include a forward-looking forecast engine. The forecast engine may use desired parameters as the input data to create future predictions. The forecast engine may run scenarios and iterate quickly to determine how to maximize (and accurately estimate) future production. The forecast engine may also be used to understand the drivers of performance and how to increase production in the future. The forecast engine may forecast future production, based on how the stockpile behaved in the past and future production assumptions. The future production assumptions may include the settings and parameters that may be planned for the near future. In other words, the future production assumptions may include the setting of parameters for how the stockpile should operate in the future (e.g., over the next year). The forecast engine may utilize the trained and tested predictive model, along with certain future production assumptions (which may be obtained from the mine plan). The forecast may use data from the mine plan (e.g., 1-5 year mine plan) such as, for example, geological exploration (e.g., data about where the sulfides (e.g., including pyrite), mixed ores and/or oxides are located in the mine map), route plan (e.g., route ore to a particular location over a period of time), irrigation plan, ore map, etc. The user may enter such mine plan data (obtained from other tools and sensors) into the system or the system may acquire such mine plan data from the tools and sensors. The forecast engine may provide forecasting and predictions about the ore that has not yet been placed and will be leached under a set of predicted conditions. The forecasting process may combine estimates from a predictive model (trained on historical data on stockpile-level copper production) with forward-looking estimates of likely values for each predictor in the model. Estimates for predictors may be determined based on the mine plan (for placements and grades), recent historical values, DUL estimation or by 'helper' models that estimate settings via a predictive approach. End users may override these settings by inputting expert-determined values or different historical data via a graphical user interface.

The forecast engine may allow inputs to create an input table such as, for example, a project identifier, a plan identifier, a forecast time period of interest, the option to use calculated data or the option to use the data from the mine plan. The pre-set options may include, for example, flow, TCu, XCu and total tonnage placed. The system may generate an input table (e.g., 5 year monthly forecast file) based on the forecast input. The user may manually enter other key inputs for the forecast.

In various embodiments, the forecast engine may include forecast input table creation logic. The system may supplement the recent values that the predictive model was trained on and the historical model input table with other data to develop the input table (e.g., future model input table) for the forecast model. Dumped sections and the future sections may include columns such as, for example, on/off dates, TCu, XCu, QLT, P80, tons and/or water-soluble Cu assays (e.g., for re-mining applications). The dumped sections may be derived from ore map data and DUL data via a DUL model. The future sections may be derived from DUL data via a DUL model, the mine plan and user inputs. The lift height may be derived from user inputs. The application rate may be derived from recent values (from the historical model input table). The raffinate chemistry may also be derived from the recent values. The Area On may receive data from the dumped sections, the future sections and the lift height. The heat soft sensor may receive the application rate and the raffinate chemistry. The flow may receive data associated with the Area On and application rate. The Lift Temperature may receive the data from the heat soft sensor. As such, the future model input table may receive input data from all (or any subset) of the above sources.

Figure 4:
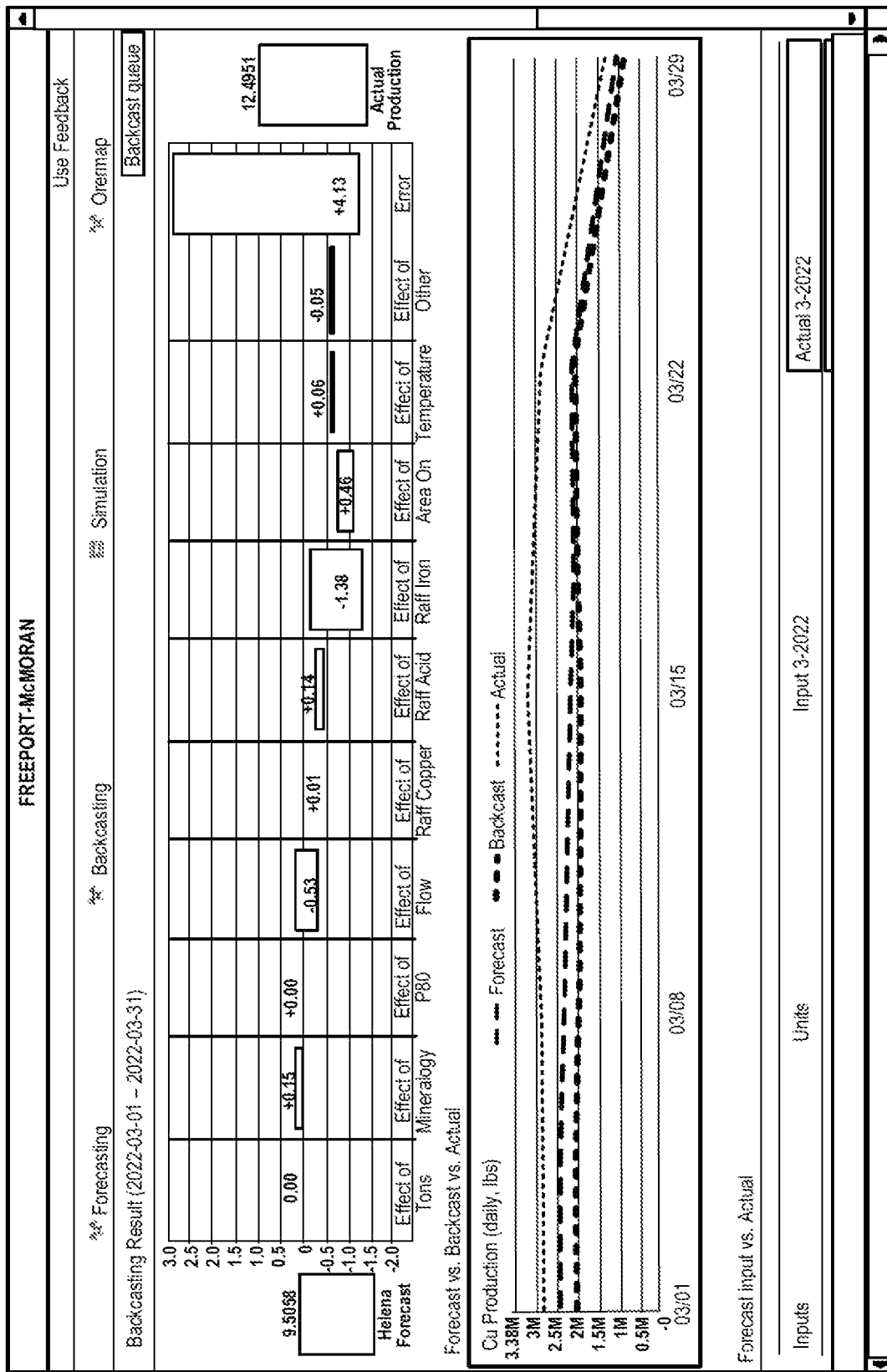
FIG. 4 is a screen shot of backcasting results along with a graph showing the forecast against the backcast and actual results, in accordance with various embodiments.
Figure 5:
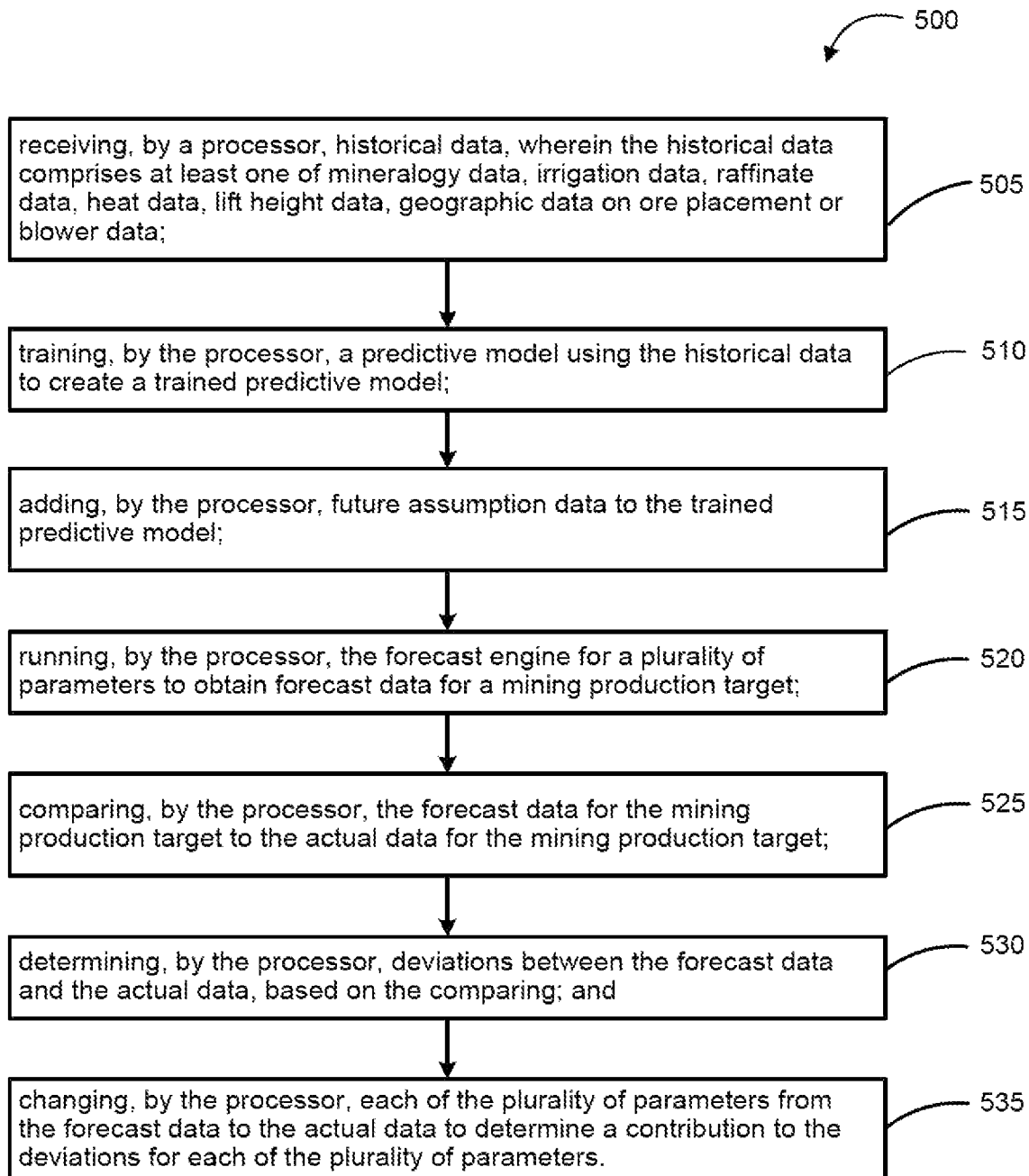
FIG. 5 is a flowchart of the overall process, in accordance with various embodiments.

In various embodiments, the system may include backcasting via a backcast engine which breaks down the sources of an error. As such, the backcast engine may be run after the period in question. The backcast engine may understand the drivers of performance, the interactions of the drivers and/or how to increase production in the future. As set forth in FIG. 4, the backcast may reconcile the forecast (what is expected to be produced) with what is actually produced. The backcast and forecast may use the same predictive model (so both the backcast and forecast learn from the same information), in order to properly reconcile the actual and predicted performance. A mine may not operate as expected due to various changes (e.g., unexpected variance in operating norms or parameters driven by human deviation from forecast plans), so the actual performance of the mine may not match the predicted performance. For example, the forecast may include 1000 pounds of copper, but the actual production is 750 pounds of copper. If any deviations exist between the output of the forecast engine and the actual data, the system may evaluate the deviations (e.g., using data science) to generate a product backcast.

The backcast may re-run the forecast, but instead of using input parameters as the input parameters were predicted to happen, the backcast may incorporate the actual input parameters that the stockpile experienced. Differences between actual production and backcasted production indicate areas of the model that may be further refined. The system may adjust each variable from the desired amount to the actual production amount. By adjusting the variables to the actual amounts, the backcast enables breaking down the deviations by specific causes. Determining the specific causes helps to determine how the predictive model and/or forecast may be changed to improve the accuracy of the predictive model and/or forecast. In the above example, the system may use the backcast and the same predictive model to determine that adjusting the days under leach may account for 50 pounds, adjusting for the head grade may account for 75 pounds, and adjusting for the raffinate flow may account for 125 pounds. Because the forecast period is already completed, the system can use observed actual information to determine which parameters to adjust to better match the desired forecast. Therefore, the backcast may determine how to adjust the parameters to compensate for the 250 pound deviation. The adjustments may be provided in a report, displayed on a screen, provided as suggestions and/or may be used to initiate practical applications. For example, the adjustments may result in sending a signal to a machine to adjust the machine's operations in line with achieving the desired production.

As another example, because raffinate iron was worse than expected in February, copper production was 1.38M pounds lower than predicted. The system may then implement adjustments to optimize production in the future (e.g., adjustments that impact raffinate iron). The system may repeatedly flag raffinate iron issues at a stockpile. The system may run different scenarios with different ferric concentrations to size the production impact for the stockpile. The system may determine that maintaining forecasted ferric concentrations results in 31.9M pounds of copper for the stockpile compared to recently observed ferric ratios. Based on these findings, the system may implement initiatives such as increasing cure acid, raffinate solution chemistry (e.g., acid concentration) or applying pyrite.

The backcast may quantify the impact of each variable for optimization. A production backcast may be generated from a reconciliation between model assumptions and actual data. The backcast may foster performance dialogs by estimating the parameter-by-parameter drivers of the gap between the forecast and actual production. The backcast may cycle through forecast values and the backcast may replace each forecast value in sequence with observed values. The backcast may re-estimate the predictions after each replacement to benchmark the role that a given parameter played in driving the production gap. For example, estimated placements may be replaced with actual placements, while all other forecast parameters are held constant. The predictions made with these inputs estimate the effect that missed placements had on driving a gap between the forecast data and the actual data. The estimated placements may be re-incorporated into the predictive model, and for example, the estimated P80 may be replaced with the observed P80. The prediction cycle may estimate the effect that the variance in the expected particle size distribution plays in driving the gap between the forecast data and the actual data. The estimated P80 may go back into the model and the iterative logic may repeat, cycling through every input into the forecast sequentially to make a comprehensive estimate of the drivers of the forecast gap.

Figure 6:
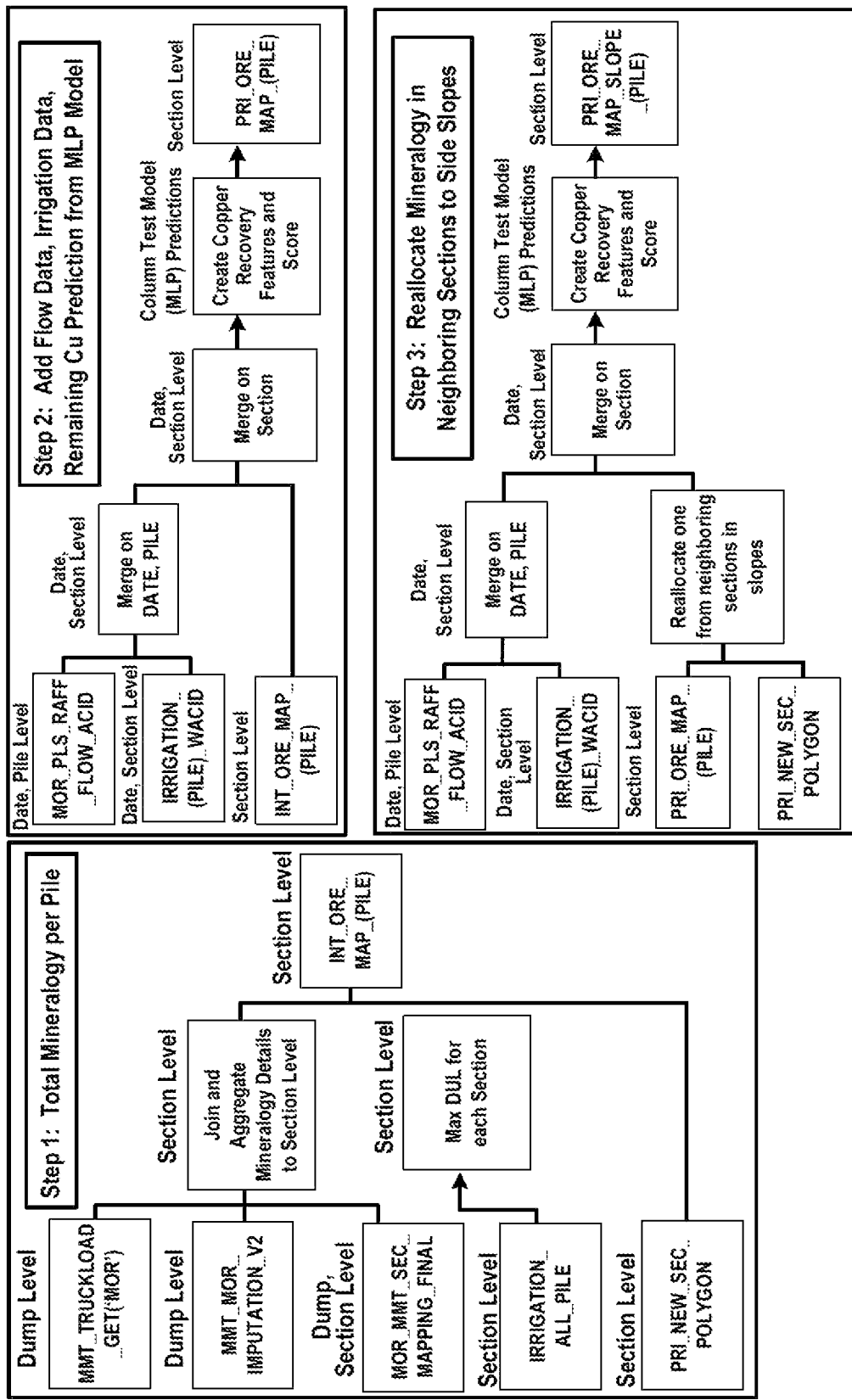
FIG. 6 is a flowchart of the data that is used to create the ore map, in accordance with various embodiments.

The ore map may not only determine the ore that has been placed, but the ore map may help target economic pockets of old copper for recovery initiatives. In various embodiments, and as shown in FIG. 6, the ore map may include ore placement targeting via dispatch data, truck sensor data (e.g., from one or more of the sensors in FIGS. 7A-7F), GIS polygon data and/or mineralogy data (e.g., from a block model). The ore map may use similar data and models to determine the amount of copper extracted through the leaching process. The ore map may also provide a visualization of where the stockpile includes recoverable amounts of copper, based on the historical leaching processes for the stockpile.

As set forth in FIG. 6, the ore map data flow may include a determination of the total mineralogy per stockpile. The system may obtain information from MMT, section mapping, irrigation and polygons. More specifically, the system may join and aggregate mineralogy details to the section level by combining the MMT truckload data at the dump level, the MMT imputation data at the dump level and the MMT final section mapping data (combination of MMT, haul truck sensor and dispatch) at the dump level or section level. The system may also obtain the maximum DUL for each section at the section level by using the irrigation data (raffinate flow, quantity, time, etc) over all stockpiles at the section level. The intermediate ore map for a stockpile may combine the section level aggregation of mineralogy details, the section level maximum DUL for each section and the primary new section polygon.

The ore map data flow may also include the addition of flow data, irrigation data and remaining copper prediction from an MLP model to obtain information by section and by date for a stockpile. The system uses data about where the copper is from, where the copper is placed and where the copper is remaining. The system may merge on the date and stockpile at the date level and section level by combining the PLS grade and flow and/or chemistry (e.g., acid) concentration at the date level and stockpile level with the raffinate irrigation on a stockpile at the date level and section level. The system merges the date and stockpile, so the system can provide raffinate chemistry data and irrigation data at the date level and understand the impact on the section on that date. The merge on section at the date level and section level may combine the merge on data and stockpile with the intermediate ore map for a stockpile. The merge on section may be used to predict the estimated copper recovery (and score) using a column test model with MLP predictions. The estimated copper recovery (and score) may be used by the primary ore map for a stockpile at the section level.

The ore map data flow may further include reallocating ore in neighboring sections to the side slopes. The system may merge on the date and stockpile at the date level and section level by combining the raffinate flow and acid content at the date level and stockpile level with the irrigation on a stockpile with acid content at the date level and section level. The system may reallocate the ore from neighboring sections to slopes by combining the primary ore map for a stockpile at the section level with the primary new section polygon. The merge on section at the date level and section level may combine the reallocate the ore with the merge on data and stockpile. The merge on section may be used to create the copper recovery features and score using a column test model with MLP predictions. The system may merge on the date and stockpile at the date level and section level by combining the PLS grade and flow and/or acid concentration with the raffinate flow acid at the date level and pile level with the raffinate irrigation on a stockpile with acid at the date level and section level. The copper recovery features and score may be used by the primary ore map slope for a stockpile at the section level.

The ore map may also include 4D visualization, including x,y,z and time information. The ore map may provide interactive visualization of all (or any subset) stockpiles, section mineralogy populated on the map of each stockpile, filtering of sections by lift, stockpile or mineralogy composition and/or displaying aggregated values for selected sections. Ore Map 4D visualization (aka "ore finder") may include determining x, y, z locations of the remaining copper and time-series layering. The ore map may define stockpile and section boundaries based on polygons recorded in GIS. Dump locations of haul trucks may be mapped into these polygons based on combined signals from MMT location information (which obtains information from a beaconing system), GPS coordinates pulled from sensors and other systems on haul trucks and mapping section identifiers and sub-piles to specific leach stockpiles. After the dump locations of trucks are known, the MMT data (associated with all trucks matched to a given section) are aggregated and averaged to estimate section-level characterizations of mineralogy and P80. Recovery from these sections may be estimated based on the column test model, and the remaining copper may be calculated at the section-level by deducting estimated recovered copper from initial placements. Finally, the system may determine which sections are economically viable for recovery via drip, wobbler or injection irrigation based on a number of contiguous high-remaining sections and the proximity of the high-remaining sections to a top lift.

In various embodiments, the column tests may use column test modeling to leverage machine learning (e.g., a deep learning architecture) applied to lab copper leach tests to estimate recovery. The ore map may further include data from a column test predictive model which may include applying deep learning to copper leach tests. The column test predictive models may be trained on laboratory records of column test performance. The predictors may include mineralogy, solution chemistry (e.g., acid concentration) and raffinate flow. Solution chemistry may include any chemical constituent or any chemical property (e.g., bio). The predictors may also include temperature, the introduction of air and/or the addition of leach enhancing additives, microbes, or catalysts. The estimates obtained from these column test predictive models may serve to estimate section-level recovery in the ore map.

The chemistry data results from an assay of the column test may be stored in a laboratory information management system (LIMS) that may manage the collection, processing, storage, retrieval, and/or analysis of information generated in laboratories and/or in the mines. For example, the system may use StarLims as its LIMS. The mineralogy data of the column test may be stored in another database. The column test simulates leaching in a section (or column) of ore in controlled conditions. The controlled conditions include adjusting different process parameters applied to the column of ore. The controlled conditions may result in increasing the accuracy of the chemistry data and mineralogy data to be used for modeling. A multi-layer perceptron (MLP) may receive the days under leach data, chemistry data and mineralogy data from the leach column tests to build a column test predictive model. The MLP is a neural network that is used in the ore map tool to determine the estimated remaining copper in a section of a stockpile. In particular, the MLP uses geologic data and mineralogic data to determine a location in the section of the stockpile the production occurred from and what is left in the stockpile. The column test may provide output data for use in the MLP. The output data may include, for example, the recovery kinetics (e.g., days on leach) of copper or the amount of acid consumed. The input data for the column test may include, for example, raffinate Fe (may include $Fe^{2+}$ feature), raffinate acid, raffinate $Cu^{2+}$, XCu, QLT, application rate, cure acid (e.g., ORP), temperature and/or the use of additives, microbes, or catalysts. With regard to the cure acid, the MLP may include agglomeration acid concentration which is applied in column tests and used for mine for leach (MFL) processes.

The system may provide the chemistry data and the mineralogy data to the MLP to build a column test predictive model. The system may determine, using the MLP, the estimated remaining mineral in the section of the stockpile based on the column test predictive model. The system may transmit the estimated remaining mineral in the section of the stockpile to an ore map. The system may train the column test predictive model on laboratory records of column test performance. The system may generate a mineral recovery prediction from the MLP. The system may generate, using the mineral recovery prediction, a mineral recovery curve to estimate mineral recovery from leaching over a period of time.

A simple neural network may include an input layer, a hidden layer and an output layer. The hidden layer may include several small decision nodes (called neurons) that independently model data. Each neuron has input data and output data as parameters. A synapse is a connection between two neurons and has a weight as its key parameter. The final outputs may be determined by weighting information obtained from each neuron in the hidden layer. The system may also use deep learning which is a network of neural networks that learns in phases. The information may be pooled to find higher-level features that are ingested by the next layer. The deep learning may use a large amount of data to achieve strong performance, but the results may be complicated to interpret when the networks are excessively deep.

The block model provides an understanding of ore placements into the stockpile. In. various embodiments, the block model may use drill hole data to map the location of the ore (e.g., in 3 dimensions), head grade, clays, geologic data and/or mineralogic data. The drill hole data may be used determine blast size, blast pattern and a blast plan. The blast does not excessively disrupt the ore, so the location of certain mineralogic areas is still known (e.g., high grade ore area, low grade ore area, high clay area, etc). The locations of those mineralogic areas may be associated with different shovel loads, truck loads, etc. For example, the system may have data about a specific truck on a specific day obtaining ore from a particular location, and that ore has certain mineralogic features. Based partly on the haul truck sensors and the dispatch system, the system may have data about where the ore was obtained, where the ore is placed in the stockpile, when the ore was placed on the stockpile, the order that the ore was placed on the stockpile and other data about the ore. As such, system includes a full block model of the final placement tracking system.

The geologic block model may obtain information from drilling, assaying, geotechnical work, mapping, etc. to help determine conditions. Geo-statistics and tools may interpolate and extend values into all pertinent blocks. The block model may include a spatially correct database of the geology information based on sampling and geologic interpretation. Each block may maintain many items that are coded with quality (e.g., metal grades, type of materials, lithology, alteration, etc.) and quantity (e.g., densities, topographic completeness, structures, etc.) codes and information. The block model may visually display the block model grades and HPGPS (high-precision global positioning system) dig points. As such, the block model may include adding value in block models based on analytics output and turning "waste" stockpiles into economic reserves.

The block model may provide coordinates for the ore. The ore may be drilled and blasted, then the system re-maps the ore in the block model based on how the ore may have been moved in the blast. The system may provide the data about the new location of the ore and the contents of the ore to the shovel which will load the ore into large haul trucks for transport to appropriate destinations. The system may also include the capturing of dig coordinates with each scoop of the shovel bucket, so the shovel or system can determine if a certain ore section is in that particular scoop. The system may use CAES (computer aided earthmoving system) products called Terrain or ProVision to obtain the scoop data. The system or shovel may determine where the ore should be placed based on the contents of the ore in the scoop, after the ore is scooped up by the shovel. For example, the system may determine that a first ore scoop with more copper content should be placed in a first truck that is scheduled to go to a particular leach stockpile, while a second ore scoop with less copper should be placed in a second truck that may be scheduled to go to a mill or different area.

In various embodiments, the system may use different variables and engineering features as inputs to the predictive model to improve leach efficiency and impact leach recovery. The leach recovery directly influences mine operating costs and ore routing decisions. For example, if conditions are not ideal and copper recovery is poor, the cost to recover a pound of copper from a ton of ore increases. The costs of mining, transporting, and placing the ton of ore on a heap leach stockpile may not be overcome if an insufficient amount of copper is extracted from that ton of ore. Inversely, when heap leach recovery is optimized, more copper is recovered from each ton of ore placed and profitability improves. If the cost of heap leaching (dollars per pound of copper recovered) is too high and if the mineralogy is appropriate, it may be economically advantageous to route that ton of ore to a froth floatation and smelting process to recover the copper. If the grade of the ore is too low to justify processing costs that would be incurred either by leaching or froth flotation, that scoop of ore may be routed to waste.

For a stockpile, the system may obtain raw data inputs such as, for example, raffinate flow acid, polygon selections (e.g., ArcGIS), weather, truck load (e.g., from MMT), truck dump locations (e.g., from the dispatch system), grade (e.g., from mine plan and load information) and/or section mapping. The truck load, truck dump locations and grade raw data may be subject to feature creation and feature cleaning via imputation. Imputation may include replacing any missing values with an estimate (e.g., from dummy sections), then analyzing the full data set as if the imputed values were actual observed values. Irrigation data (e.g., irrigation stockpile with acid) may be added to the polygon selection data. The imputed data may be combined with raw section-level mineralogy data for a stockpile. Raffinate flow acid for a particular stockpile may be added to the raw data for the raffinate flow data. The system may repeat a similar process for additional stockpiles.

The potential predictive variables for leach production may be found in different areas such as mineralogy, irrigation and raffinate. The potential predictive variables may also include new features such as heat, lift height and blowers. Experimenting may help determine such new features that improve model performance. The potential predictive variables for mineralogy may include, for example, TCu percentage, XCu percentage, QLT percentage, P80 size and tons. The predictive model may leverage either XCu or QLT depending on which is the most performant. The potential predictive variables for irrigation may include, for example, raffinate application rate, area under irrigation and/or DUL. The potential predictive variables for raffinate may include, for example, raffinate flow rate, raffinate chemistry (Cu, Fe, $Fe^{2+}/Fe^{3+}$), raffinate acid, cure acid, and/or the concentration of any leach enhancing additives. The potential predictive variables may also include, for example, ambient temperature, days under leach, slide slope irrigation, wobbler v drip, ore permeability, precipitation, ground temperature and/or ore hardness. The system may include a variable such as venting to aerate the raffinate.

The system may try to make the predictive models for different stockpiles more similar, so the system may collect data about the different stockpiles based on the similar predictive models. If a first stockpile has similar features as a second stockpile in a different location, the system may take a similar predictive model that was used for the first stockpile and use it for the second stockpile. The system may also use the similar models to determine how changing parameters or environmental conditions at different stockpiles may impact the leaching process. As such, the system may use the predictive models to standardize the approach and improve comparability between different stockpiles.

A distinguishing factor between a copper bearing mineral and an economic copper ore is the economic benefit that can be derived from extracting value from processing the material. The copper grade is a factor in this analysis. The copper grade is the amount of copper present in each ton of rock. The copper grade is often expressed as a percentage of total copper present. While knowing how much copper is present in the rock is a good indicator of economic viability, the amount of copper present in the rock does not necessarily tell the whole story. The copper mineralogy is also important, as well as the relative amounts of other valuable minerals that may be co-extracted with the copper. The amounts and values of economically important elements can be mathematically combined with the amount of copper to provide a copper equivalent grade. For example, when molybdenum sulfide is present in an orebody and can be co-extracted with the copper in the froth flotation process, the copper equivalent grade can be expressed as: Grade Copper Equivalent=% Cu+C*% Mo, where C is a factor based on the economic value of molybdenum in any current market conditions. Therefore, the copper equivalent grade of an ore that contains metal values in addition to copper can change according to commodity markets. This is important to ore routing because, while froth flotation is able to recover molybdenum in the form of the naturally occurring mineral molybdenum disulfide, leaching processes are typically not able to recover molybdenum. Likewise, the precious metals (e.g., gold, silver and platinum) may be recovered by froth flotation and smelting processes, but such precious metals may not be recovered by heap leaching. As such, the processes, mechanics and economics of ore routing may be optimized by utilization of models, simulators and engines that are adjustable according to metal pricing and market conditions. Ores that contain un-economic percentages of copper are said to be "below-cutoff-grade" materials. Because the processing cost via froth flotation and smelting is higher than that for heap leaching, ores that are below the "mill cutoff grade" may often be economically processed via leaching.

In various embodiments, the dispatch system may be used for tracking equipment status and/or position. The dispatch data may be used in the MMT and/or the Rules-based Matching. The dispatch system may also include cycle optimization (e.g., routing and scheduling based on mine plans as well as capacities of crusher, etc.), balance idle equipment times, balance queue times, manage fuel, operator's performance, productivity, etc. A typical haulage cycle may include receiving truck loads from the assigned shovel, traveling with a full truckload to an assigned dumping location, arriving at the dump queue, dumping the load, traveling empty back to the assigned shovel, arriving at the shovel queue, spotting, and then the cycle may repeat. The haulage cycle data may include a shovel identifier, a shovel location identifier, a truck identifier, a load time and data and a stockpile identifier. The spotting may be the appropriate locations for the truck to be able to receive the ore from the shovel or the appropriate locations for the truck to be able dump its load in the appropriate section.

Rules-based matching is used to analyze two or more inputs about where a haul truck may have placed a load. A dispatch system (e.g., Modular dispatch system) may include a beacon system that may provide data about the time a truck arrived at a certain location and dumped a load. The dispatch system may set a beacon many miles away from the dump location based on how the stockpile or lift may be configured. The truck sensor may provide data about a truck dumping a load at a particular location (e.g., latitude, longitude and elevation) and at a particular time. The truck sensors may include one or more sensors that may be added to trucks by the original equipment manufacturer (OEM), added to the trucks by the OEM based on a customer request and/or added to the trucks by a customer. For example, some trucks may have over 350 different sensors (e.g., FIGS. 7A-7F set forth a list of some of the sensors) that provide data about different aspects of the truck and its actions. The sensors may include GPS sensors that provide GPS data about the location or movement of the truck, load sensors that may track the weight of the load, dump sensors that may track the bed position, energy sensors that may track the amount of energy (e.g., gas, propane, electric, etc) stored in the truck or being used by the truck, gear sensor that may monitor that gear placement in the truck, a brake sensor that may monitor when the emergency brake is set, etc. The system may also include soft sensors. A soft sensor (software sensor or virtual sensor) may provide an indirect measurement using a combination of process data (input) and a model that uses the input data to predict a target quantity (output). The input data used for the prediction may be composed of signals from hardware sensors and actuators. The soft sensor may process several measurements together using control theory.

The system may use rules to determine that a dump occurred based on, for example, the truck not moving (or speed below a threshold), the truck gear is in park, the emergency brake being set and the bed position passing a threshold height. The system may presume that the truck sensor data is accurate, unless the system determines (e.g., based on a series of rules) that the sensor is broken, a sensor is not located on the truck and/or the dispatch location should be trusted instead. If the system determines that the sensor data and the dispatch data may not be sufficiently accurate, then the system puts the truck load in a dummy location. The system may use the dummy location to account for the load being dumped, but the system may not know precisely where the load was dumped.

Mine vehicles (e.g., haul trucks) typically include a sensor (e.g., OEM sensor) that provides GPS readings. GPS sensor readings may provide the x, y, and z coordinates of vehicles making dumps to a particular lift on a stockpile. The sensor may be read at a time preceding the dump (e.g., 30 seconds before the dump) because the sensors are more accurate while the truck is moving. In various embodiments, the coordinates may be aggregated and averaged in order to determine the physical location of the vehicle as it approaches and then dumps the ore. The elevation data may be used to determine the elevation of the lift. Deducting the analogous elevation measurement from the prior lift provides a mechanism to calculate stockpile (or top lift) height from sequential measurements of the lift heights in the stockpile. For crush-for-leach stockpiles, the lift height may be set by the conveyor height, wherein the conveyor may have a sensor that provides the conveyor height to the system. The ore map may be used for conveyor stacked stockpiles and may include conveyor location data, belt sampler data, etc.

Because trucks travel across the top of the lift of the stockpile that they are building, the further aggregation of measurements from multiple vehicles serves to estimate the boundary of the stockpile's top lift. For example, the system may determine the paths traversed by each truck and form a boundary around all of the paths, and the truck path boundary may estimate the boundary of the stockpile's top lift. In various embodiments, the system may revise the boundary elevation over time using sensors that measure points on the surface or interior of the stockpile.

In various embodiments, the aggregated x, y, z information from the trucks may be compared with defined GIS Polygons and dispatch information to provide more accurate dump location precision. Such a comparison may be helpful to improve the accuracy of the dump location due to potential errors from periodic overlap in polygons, dispatch recording a different beacon dump location, or other manual dump location entry errors. A polygon feature may be a GIS object that stores its geographic representation as one of its properties (or fields) in the row in the database. The geographic representation may include a series of x and y coordinate pairs that enclose an area. A geographic information system (GIS) is a computer-based tool for mapping and analyzing things that exist and events that happen on Earth. GIS technology integrates common database operations such as query and statistical analysis with the unique visualization and geographic analysis benefits offered by maps.

With respect to stockpile and section mapping, in general, the system may receive the dump location information (e.g., from MMT and truck sensors). The system may combine the dump location information with GIS polygons. The GIS polygons include information about the section of the stockpile that the load was dumped, including name, characteristics, physical location in x, y, z space, etc. Thus, the system provides information about where in a stockpile the dumped ore exists (and may exist in perpetuity until re-mined in the future). Based on this information, the system may provide a map of (and target) a specific section in a specific stockpile and at an x, y, z location that a truck dumped ore. The system may build a composite of all of the dumps inside this section of this stockpile.

More specifically, for each stockpile, the system may obtain the MMT section mapping data table by combining or joining the MMT truckload data to get the dump location, the location data to obtain the x, y coordinates for each dump location, the dump data to get the GPS x, y location from dispatch and the section data to get the section polygon. The system may combine the MMT section mapping tables from stockpiles in a mine into a MMT section mapping dispatch data table for the mine. The system may obtain the MMT section mapping haul truck data table by combining or joining the MMT truckload data to get the dump location, the location data, the dump data to get the dump identifier, the section data to get the section polygon, the haul truck idle at dump data to get the dump start and end timing and the sensor fixed interval data to get the haul truck GPS longitude and latitude. The MMT section mapping for a mine may combine the MMT section mapping dispatch data table, the MMT section mapping haul truck data table and the haul truck GPS status (that provides GPS quality). The system may preform a preprocessing step to handle sections with overlap. The system may combine the data into different tables such as, for example, the section polygon table, the dump location lift map (dispatch) and the haul truck dump location based on GPS. The haul truck dump location based on GPS may be sent to a haul truck (sensor) section mapping. The section polygon table and the dump location lift map may be combined into a dispatch section mapping table. The MMT section mapping table may be a combination of the dispatch section mapping table and the haul truck (sensor) section mapping.

In various embodiments, the system may use ore characteristics as inputs into the predictive models and to determine the type of ore in each shovel load. The ore characteristics may include ore quality and ore grade. Ore quality may include, for example, total copper, acid soluble copper, QLT, P80, iron values, clay values and/or pyrite values. Ore grade may include, for example, total copper and acid soluble copper.

The size distribution of the ore is a factor in determining how much copper can be leached from the ore. Ores with very high copper contents on the order of 3 to 4% copper have a high enough value that the ore can be finely ground and leached in stirred tanks. In this case, nearly all the mineral grains in the ore are liberated and available for contact by leach solutions. However, ores with such high metal contents are rare. More commonly, leach ores contain between 0.1 and 0.5% copper and leaching is handled at the most economically advantageous particle size. While the P80 size is commonly used to provide one number that nominally represents an entire size distribution, this simplified method has drawbacks. Most notably, the P80 does not tell the proportion of fine particles that are present. Fine particles present in heap leach structures may migrate and plug up solution flow channels, blinding portions of the heap off from contact with leach solutions.

In various embodiments, the system may also include any size distribution model that helps to describe the impact of particle size on recovery. For example, the system may incorporate a model that relates copper recovery to size distribution. The data to build such a model may be acquired from leach column testing and pilot testing. In these tests, ore of the same mineralogy and textural attributes is blasted or crushed to different size distributions. For example, a split sample of Run of Mine ore with a P80 of 8 inches could be loaded into large diameter columns and leached to obtain a certain recovery after a given number of days. Another split could be crushed to a P80 of 6 inches and column tested in an identical way. Other splits of the same sample could be crushed to different particle size distributions and leached. Because both the ore and the leaching method are similar, any statistical recovery differences may be attributed to a change in particle size. This change in recovery by particle size distribution could be expressed mathematically and incorporated into the system either alone or in combination with other factors such as mineralogy and grade. Such a model may be somewhat ore-specific because mineral particle sizes and rock type associations vary from ore to ore, but as a library of ore types and rock types is expanded, such a model may provide valuable information. In crush-for-leach operations, the particle size distribution may be set by adjusting the crusher setting and the particle size distribution may be checked by size analysis of periodic belt samples. For Run of Mine ores that are not crushed prior to leaching, size analysis may be obtained by data image analysis from cameras on ore shovels. Such particle size distribution data may be used in the system.

The SDR (size distribution reporting) solution enables the reporting of size distribution metrics for material that is being shoveled, blasted and/or mined. The SDR is often called ShovelCam, Split Cam or Frag Cam. This SDR application may be used for capturing fragmentation data at the shovel loading location. Images of the mining face may be captured by cameras mounted onboard the shovels. In various embodiments, the images may be sorted and processed using Split-Online fragmentation analysis software to obtain the measured real-time size distribution of the material being loaded, and the results logged to a database. The cameras may be used to obtain the real-time size, instead of measuring the size of the rocks in the field. In various embodiments, the system may determine mineralogy by taking the spectral analysis of a truck load. The system may determine the size of the rock to meet the P80 ($80^{th}$ percentile). For example, the size of the rock may be 6 inches or smaller to meet the P80. As such, the SDR may be used to identify trends in the rock size after the blast and improve the management of the blast fragmentation practices. The system may receive the SDR data to determine appropriate adjustments for the blasting process to meet the target P80. Such adjustments may include, for example, the hole spacing, hole depth, powder factor, burn, etc. The system may send signals of these adjustments to a blasting system that may implement future blasts. Reports feed from the EDW (enterprise data warehouse) that include a "Global Drill and Blast" database. This data may be integrated with data from MMS PowerView as well as CAES/Terrain.

The application rate may be the amount of the raffinate irrigated onto the stockpile as a function of the total flow of the raffinate solution over the total area being irrigated. The raffinate application applied to the ore may be determined for each lift. In various embodiments, the system may use flow rate (acquired from skids or flow meters) and leach area (acquired from ArcGIS) with acid concentrations (acquired from acid addition volumes to raffinate and lab assays) to calculate how much acid is applied to the ore. The amount of acid applied to the ore may impact the ore map, which may serve as a feedback loop for adjusting the mine plan.

The cost of sulfuric acid used for leaching is both significant and variable. Leach recovery may be highly dependent on exposing the ore to the optimum amount of acid so that the copper is put into solution. However, over application of acid causes increased acid consumption by gangue minerals (gangue acid consumption), degradation of the ore, and decreased heap permeability. Therefore, the system may incorporate models for raffinate application. Such models may also provide cost savings for mine (e.g., leach) operators, as the mine operators may be able to extract the maximum value for each volume of ore without wasting acid. In addition to having a specific copper mineralogy fingerprint, each individual volume of ore contains gangue minerals. The types and relative amounts of specific gangue minerals determine the amount of acid each block of ore may consume, in addition to the acid consumed to leach the copper minerals. Because leaching may be driven by the amount of free acid in solution, a percentage of the gangue acid consumption may be used to create localized conditions which promote copper leaching. In various embodiments, the system may include a model that allows a more targeted addition of acid to the ore. A more targeted addition of acid may be particularly feasible in the case of acid addition to agglomeration where signals from a system (e.g., an over-the-belt analyzer) may be used to control acid addition rates to agglomeration depending on the mineralogy of the ore being treated.

The acid that is applied to the ore may be introduced as a component of the raffinate flow. Thus, the acid that each particle of ore sees is a function of the acid strength of the raffinate, the flowrate of the raffinate (application rate), the days the ore is under leach, and the physical and mineralogical characteristics of the adjacent ore particles (particularly those particles spatially above the particle in question). For example, if the ore spatially above the particle in question has consumed a significant portion of the free acid that was applied to the ore, there may not be a sufficient driving force for leaching to continue. If the leach driving forces are not present throughout each volume of ore under leach, then the mining, haulage, and placement costs for that volume of ore may be wasted. However, the acid should not be over-applied, or else the acid may be wasted and permeability concerns occur.

In various embodiments, the system may include a model that estimates the manner in which acid bearing raffinate travels through leach ore, based on a method of estimating acid percolation via Darcy's Law. Darcy's Law may provide an indication of how far leach solutions travel through the pad in feet per day. The acid percolation may also be determined by using tracers (e.g., a material or liquid that may be added to the acid and can be monitored or trace as it percolates the ore). This system may leverage any suitable code (e.g., Python code) to estimate percolation from estimates of ore porosity, particle size (as measured by P80), and irrigation flows (as estimated by sensor readings) to estimate the percolation of raffinate through a leach stockpile. Darcy's law states the principle which governs the movement of fluid in the given substance. The Darcy's law equation describes the capability of the liquid to flow via any porous media like a rock. Darcy's law is based on the fact that the flow between two points is directly proportional to the pressure differences between the points, the distance, and the connectivity of flow within rocks between the points.

Measuring the inter-connectivity is known as permeability. To understand the mathematical aspect behind liquid flow in the substance, Darcy's law can be described as the relationship among the instantaneous rate of discharge through porous medium and pressure drop at a distance. Using the specific sign convention, Darcy's law is expressed as: $Q=-KA\, dh/dl$, wherein Q is the rate of water flow, K is the hydraulic conductivity, A is the column cross-section area and dh/dl indicates a hydraulic gradient. The various Darcy's law factors may be measured with appropriate sensors. The system may use the data provided by Darcy's law to determine, for example, if a reagent should be added to the leach stockpile to help increase the percolation and improve leaching.

Another factor for determining how much copper may be leached from a heap leaching operation is the amount of surface area that is turned on (e.g., under leach) at any one given time. There are certain time periods during which a given section of ore will not be under leach. At the beginning of the leach cycle, the ore may not be under leach while the ore is being placed on the leach pad by conveyor stackers or haul trucks, which is often the time that solution delivery pipes and leach lines are being laid. During the leach cycle, there may be times when raffinate flow is turned off purposely. For example, "pulsed leaching" may be beneficial for certain copper ore mineralogies which may benefit from short rest periods which allow stockpile temperatures to rise. At the end of the leach cycle, leaching is turned off so that leach pad surface can dry out enough for people to walk on and so leach lines and piping can be stripped from the pad. During regular leaching, there are also times when a certain portion of the ore may not be receiving raffinate because leach lines are plugged or because there is a leak in the raffinate distribution system.

The system may determine the ore age in the stockpile based on leach rates. Leach rates may vary throughout the leach cycle with ores leaching faster at the beginning of the cycle than at the end. In various embodiments, the system may track when each section was turned on and how many days each section has been leaching. This data may be aggregated for all sections under leach to predict how much copper production to expect on any given day.

To analyze and diagnose the raffinate distribution problems (e.g., plugged leach lines), pressure/flow skids may be used. In various embodiments, the system may use pressure/flow skids to provide data on flowrates, pressure, flow, and raffinate distribution. The skids allow the calculation of accurate irrigation rates (gpm/sq ft) for input to the raffinate application rate feature. The system may automatically adjust valves placed in series with the flow skids. In various embodiments, the system may use the data from pressure/flow skids to meet the target leach solution application rates. Because leach solutions may be the means by which acid is delivered to the leach pad, knowing the rate that solutions are delivered to the pad, along with the acid strength of the leach solutions, allows the system to calculate how much acid is applied to any volume of ore. If a line is plugged and a sufficient amount of acid is not being applied to the section of ore, the system may adjust its models to compensate for this change. The system may also use the skid data to validate the amount of acid that the system determined that the section of the stockpile may be receiving. The system may also initiate a work order or repair order if the system detects that a certain area of the pad is receiving more or less acid than the pad should be receiving because leach lines have become plugged or are leaking.

More information about pressure/flow leach skids can be found in U.S. Ser. No. 15/539,328 filed Jun. 23, 2017, now U.S. Pat. No. 9,982,321 issued May 29, 2018, and entitled "Systems And Methods For Monitoring Metal Recovery Systems"; U.S. Ser. No. 15/989,614 filed May 25, 2018, now U.S. Pat. No. 10,190,190 issued Jan. 29, 2019, and entitled "Systems And Methods For Monitoring Metal Recovery Systems". U.S. Ser. No. 16/223,760 filed Dec. 18, 2018, now U.S. Pat. No. 10,975,455 issued Apr. 13, 2021; and entitled "Systems And Methods For Monitoring Metal Recovery Systems"; U.S. Ser. No. 17/223,404 filed Apr. 6, 2021 and entitled "Systems And Methods For Monitoring Metal Recovery Systems"; U.S. Ser. No. 17/733,171 filed Apr. 29, 2022 and entitled "Systems And Methods For Monitoring Metal Recovery Systems," all of which are incorporated by reference in their entirety for all purposes.

In various embodiments, the system may include connecting thermistors (e.g., resistance-based temperature sensors) to modular and movable self-contained "skids" housing components for reading and/or transmitting temperature data over the internet into a database (e.g., cloud or warehouse). The thermistors may be inexpensive and/or disposable. The skids may contain the thermistor sensors, a data logger, an edge computer, internet connectivity (cellular), solar power, and batteries that allow for 24/7 unattended data collection. Edge computers may run the Azure IoT Edge runtime and utilize containerized applications to read the temperature data at defined intervals and transmit the data directly into a database. Collected telemetry data may be stored within a database alongside other telemetry data where the data may be made available in a consistent format for visualization and analysis in tools (e.g., Power BI) and for inclusion in data science models.

Historically, side slopes may have been ignored because of the expense of leaching the side slopes and the relatively minimal copper production in the side slopes. However, in addition to the top surface area of the pad being leached, copper production can also be increased by leaching the side slopes of leach pads. This may be completed with drip emitters, but increased leaching is sometimes completed by spraying raffinate onto the side slopes with wobblers. The amount of leach area that is turned on may be determined by surveying the leach shapes. The polygons representing the leached areas may be aggregated to determine the combined internal area for the combination of the polygons. Because drip emitters and wobblers are expected to provide different relative amounts of raffinate to the ore, data regarding the percentage (or square footage) of the section, lift or stockpile that is under drip vs wobbler may also be captured and used in the models. The system may use irrigation source data by determining the percentage of wobblers being used at the section level. The percentage of wobblers being used at each of the section levels may be used to determine the percentage of each raffinate application method for the whole leach stockpile.

In various embodiments, the side slope calculations may be used to determine where the ore should be re-distributed from the pad and into side slopes because side slopes are leached at a different time than the ore on the pad. The side slope calculations provide an estimate of how much ore is in the side slopes and its ore characteristics. Without the side slope calculations, the contribution of the side slopes would either be missed or estimated incorrectly.

Temperature is a factor in determining leach recovery as it improves both leach kinetics (e.g., days under leach) and ultimate copper recovery. It has been estimated that every increase of 1 degree C. results in an average of 0.5% improved copper production. This effect differs for different copper mineralogies. While this copper recovery increase is generally beneficial, temperature increases may also lead to increased acid consumption, ore degradation, precipitation, and resulting permeability concerns. Therefore, in various embodiments, the model may consider the various impacts of temperature on heap leaching. The heat balance for a heap leach stockpile may account for heat entering the stockpile, heat leaving the stockpile, and heat generated with or accumulated in the stockpile. Depending on its temperature in comparison with the ore in the heap leach pad, raffinate can either be a source of heat or a heat sink. Raffinate that is above the temperature of the ore can increase the temperature of the pad, while colder raffinate can cause the stockpile to cool down. The flow and temperature of the raffinate may create a heat flux with either the potential to heat or cool the leach pad. In various embodiments, the system may acquire flow readings from pressure/flow skids and raffinate temperatures at feed ponds or in piping runs. Similarly, the flow and temperature of PLS leaving the pad may be accounted for as this represents a heat flux out of the system. Heat may also enter a leach pad via solar radiation at the surface of the leach pad and this heat may be transferred some distance within the ore structure. However, heat may also be lost from the surface of the leach pad by convective cooling, evaporative cooling and radiation emitted from the surface. In some cases, this heat loss can be minimized by such methods such as, for example, covering the leach pad with plastic film or with a layer of ore or rock. Depending on the mineralogy present within the leach pad, heat can be generated by the oxidation of minerals such as pyrite, chalcopyrite, and other sulfide ores.

The temperatures of various sections of the stockpile may be directly or indirectly measured by using thermistors (e.g., temperature probes) placed within the ore of the stockpile. Placing physical heat sensors within the ore may be time consuming and difficult, and retrieving measurements from buried sensors may be problematic. Therefore, the system may use a soft sensor to estimate the temperature within a leach stockpile. The temperatures of various sections (or sub-sections) of the stockpile may be estimated using a heat soft sensor model. In various embodiments, the system may include a heat soft sensor that provides a heat soft calculation. The heat soft sensor may determine a temperature profile for a particular scenario of various process parameters. The profile may be a profile (e.g., one-dimensional profile or three-dimensional profile) looking at the stockpile from the top down and the bottom up. The profile may not consider the impacts of the side of the stockpile (e.g., heat transfer toward the sides of the stockpile). The system may allow the user to change any of the parameters that may result in a different temperature profile. The temperature profile may reflect the different temperatures at different depths of the lift. The temperature profile may also reflect the temperature changes over time. The heat soft calculation may be a series of calculations to estimate the heat transfer at the surface (evaporation, convection, shortwave and longwave radiation exchange); estimate the heat transfer within the stockpile (advection of raffinate moving down through the stockpile and advection of air within the stockpile); and estimate the heat generation within the interior of the stockpile due to exothermic chemical reactions (ex.: oxidation of pyrite and sulfide ores). This is estimated based on the percentage of pyrite, the percentage of ore minerals and an assumed oxygen utilization rate, but these assumptions may be adjusted as the system learns more from the modeling and feedback. The heat soft calculation may be coded in any suitable code (e.g., Python code) in order to offer section-level estimates of internal stockpile temperature. The system may modify the process parameters based on trend data of the heat profile. For example, if the heat profile trends indicate that the system is flushing temperature down out of the stockpile, then in response, the system may reduce the raffinate application rate which could help to retain the temperature of the stockpile.

More particularly, in various embodiments, the process parameters may include, for example, type of film (e.g., Mantos thermal film or other type of film or cover), timeframe, total depth of the lift, raffinate application flowrate (e.g., flowrate per unit area of the raffinate on the surface of the stockpile), raffinate temperature (e.g., for overall heat balance), air application rate (e.g., flow rate of air being injected per unit area and measured at the base of the newest lift, wherein the air works its way up through the stockpile and exits from the surface), air wet bulb temperature (e.g., of the air injected into the stockpile as it tends toward 100% humidity within the stockpile), evaporation percentage (e.g., of the raffinate flow rate going in at the surface), shortwave infrared radiation absorptivity (e.g., incoming solar radiation that is reflected out and absorbed at the surface), longwave absorbed infrared radiation emissivity, longwave out radiation emissivity, exotherm heat generation (e.g., rate of energy, oxidation, etc), heat transfer by convection at the surface (e.g., heat loss directly to the air or heat loss through a thermal film cover) and average temperature at the end of the timeframe. The film may include any clear film, colored film and/or coated film. The film may include a layer of insulating material which may be ore, crushed rock and/or another crushed substance.

In various embodiments, the process generally includes the system splitting the stockpile sections into a series of vertical layers (e.g., each 3 feet tall). For each layer, the system may calculate several values such as, for example, net radiation and convection for the top layer (e.g., including estimated effects of pile covers), transmission of the heat to lower layers, quantity of reagents available for oxidation of pyrite and/or chalcopyrite, amount of pyrite and/or chalcopyrite oxidized, heat created by thet oxidation and the transmission of the heat through the stockpile, cooling and/or heating from raffinate and from the raffinate transmission through the stockpile. The initial result may include a daily temperature (e.g., for every 3 feet of the top lift). The system may roll this up as a mean or median for the whole lift, or use the temperature at a particular depth. The may utilize the Stefan-Boltzman law, wherein the total intensity radiated over all wavelengths increases as the temperature increases.

In various embodiments, the inputs to the heat soft sensor model may include, for example, amount of pyrite per weight of ore to be leached; amount of chalcopyrite per weight of ore to be leached; weather (e.g., temperature); section date; raffinate flow; total area on; raffinate acid concentration; average temperature; soil temperature; layer height; total depth of lift; ore density; heat capacity of the soil; heat capacity of the soil; leach cycle days (e.g., total number of irrigation days); starting temp of ore; ore heat transfer coefficient; rate of air introduction; air temperature; raffinate temperature; heat capacity of raffinate; raffinate utilization (e.g., a percent of raffinate that can interact with the ore); feet per degree; number of cover layers; absorption of solar energy for ore or covers; convective gain and loss (e.g., heat flux which is equal to the heat transfer coefficient multiplied by the difference in temperature between a surface and the surroundings); air emissivity; soil emissivity;

albedo (e.g., ratio of reflected solar radiation to incoming solar radiation); pyrite oxidation rate (e.g., a function that can be modified according to lab work); pyrite heat of oxidation reaction; chalcopyrite oxidation rate (e.g., a function that can be modified according to lab work).

In various embodiments, the heat soft sensor model may use the input in the following exemplary ways. The system may cumulate the amounts of pyrite and chalcopyrite for each modeled section of a leach stockpile. The system may also accumulate weather data for the timeframe being modeled. The system may average the ambient temperature over the timeframe being modeled. The system may also average the soil temperature over the timeframe being modeled.

In various embodiments, the system may incorporate various calculations that can be iterated from one layer to another layer in the heap and/or used in finite element fluid dynamic modeling. The calculations may include one or more of the following. Application rate=Section raffinate flow/total area with flow turned on; Temperature of additional layer=layer height/feet per degree; Available oxygen calculated from rate of air blown into the stockpile per time; Available acid calculated from the raffinate application rate and acid concentration of the raffinate; Net radiation=ground heat flux+latent heat flux+sensible heat flux; Net Radiation for an ore layer over a period of time=(net radiation*time)/(layer height*ore density)/ore heat capacity; Convection=convection heat transfer coefficient taking heap covers into consideration*temperature difference; Convection for a top ore layer over a period of time=(convection coefficient taking heap covers into consideration*time)/(layer height*ore density)/ore heat capacity; If more pyrite is present than the amount of oxygen needed to oxidize it, then the system may determine that oxygen is limited; If more oxygen is available than pyrite to be oxidized, then the system may determine that pyrite is limited; If days under leach is less than the time for total pyrite oxidation, then the system may determine that time is limited; Amount of pyrite oxidized=f(minimum of oxygen amount, pyrite amount, days under leach); Temperature gain due to pyrite oxidation=(pyrite heat of reaction*amount of pyrite present)/(layer height*ore density)/specific heat of ore; If amount of acid available is less that the chalcopyrite to be oxidized, the system may determine that the reaction is acid limited; If the amount of chalcopyrite is less than the acid available, the system may determine that the reaction is chalcopyrite limited; If the days under leach is less than the time for chalcopyrite passivation, the system may determine that the reaction is time limited; Amount of chalcopyrite oxidized=f(amount of acid available, amount of chalcopyrite available, chalcopyrite oxidation rate); Temperature gain due to chalcopyrite oxidation=(chalcopyrite heat of reaction*amount of chalcopyrite present)/(layer height*ore density)/specific heat of ore; Raffinate final temp=f(ore heat transfer coefficient, time, raffinate flow rate, heat capacity of raffinate, current raffinate temperature difference with raffinate in adjacent layers); Raffinate heat flux=(raffinate flow rate*heat capacity of raffinate)*(raffinate final temp−current raffinate temp); and/or Temperature change from raffinate=raffinate heat flux/(layer height*ore density)/heat capacity of ore.

Copper leaching typically occurs when chemical and physical driving forces are present. The system may receive inputs about the contribution of additives to leach recovery. In various embodiments, the ore may be sufficiently wetted that lixiviants can contact the mineral surfaces. This wetting is completed by aqueous solutions which may contain a combination of water, reclaimed water, raffinate from solvent extraction plants, sulfuric acid, and ILS (Intermediate leach solution). ILS may comprise mixtures of low grade PLS solutions which are being recycled to leaching in order to satisfy water balances. ILS is often enriched with sulfuric acid. Oxides and simple carbonate minerals may be leached simply by contact with low pH solutions containing sulfuric acid. Copper may be leached in response to the solution pH being low enough directly at the mineral surface. However, competing acid consuming reactions from adjacent gangue minerals may drive pH up to the point where an insufficient or ineffective chemical driving force is present and copper leach recovery may suffer. Sulfide minerals may be more complicated to leach and include the use of not only low pH, but elevated oxidation potential in order to leach. Achieving an elevated pH (ORP—oxidation reduction potential) may include the presence of an oxidant in solution. Traditionally, this consists of ferric iron which is generated by the aeration of solutions or the presence of native iron oxidizing bacteria (bioleaching). When iron is present in solution, the pH should be below about 3 directly at the mineral surfaces. If pH is allowed to increase because of the presence of acid consuming minerals, iron may precipitate out of solution as a sticky jarosite that can coat and passivate mineral surfaces. Alternate oxidants include halide ions such as the chloride contained in brine or solid salt, chemical oxidants, air or oxygen which may be introduced by enhancing the dissolved oxygen in solution or by the addition of stable microbubbles to leach solutions. When mineral surfaces passivate by the formation of elemental or polysulfide layers, additives may be used to alleviate this passivation. For example, the presence of silver ions in solution may restrict the formation of passivating layers on the chalcopyrite mineral surface. Another class of additives (added as solid particles) enhances galvanic leach reactions and causes corrosion and dissolution at the copper mineral surfaces. Pyrite particles may set up such galvanic reactions. Additionally, the oxidation of pyrite may provide a heat source which increases the temperature of the leach stockpile.

The ore finder may be the user interface for the ore map, and the ore finder may allow a user to determine which sections of the stockpile still have remaining copper. As such, based on the ore finder showing sections with residual copper, the system may instruct other components or machines to perform deep raffinate injection to target leach solutions with enhanced chemistry to areas of the leach pad with the residual copper found with the ore finder. To accomplish this, the system may instruct the machines to drill holes at a depth to target unleached ore. Leach solution chemistry may be tailored to the mineralogy of the residual copper and leach solutions may be pumped under pressure into the deep raffinate well. For example, raffinate solutions may be enhanced with sulfuric acid and/or another acid, ferric ions and/or another oxidant, air bubbles, oxygen bubbles, heat, microbes or any other beneficial additive.

Various other data obtained from engineering features may be used by the system. Blower data may include the ambient temperature plus the temperature change with the blowers on. In various embodiments, the temperature change may be derived from the exit temperature out of the blower that is detected by a sensor on the blower. The blower data may also include status data about the blowers being on or off. In various embodiments, the status data may also be inferred from an additional thermocouple reading, wherein if the temperature difference between the ambient temperature and the exit temperature is above a threshold, then the system presumes that the blower is on. On average, the air exiting the blowers and entering the leach stockpile may be about 25 degrees F. hotter than the ambient air. The hotter blower air increases the heat to leaching overall and acts as a heat source to the leach stockpile.

In various embodiments, the irrigation data may include an "area on" calculation that may be used to determine the share of area of a stockpile being irrigated. Mapping to create a polygon map may be completed by ArcGIS. However, in some cases, the polygons overlap which may cause certain areas of the pad to be counted twice. In various embodiments, the polygon map may correct for the double counting and create unique shapes of the overlap portion for which the ore characteristics are known. The system may determine the leach history of each unique shape by estimating the copper which may be remaining in the shape. This remaining copper estimate data is used in the ore map. The ore map may keep track of the location of potential residual copper which may be recovered at some point by targeted methods (e.g., deep raffinate injection).

In various embodiments, the system may determine the Ferrous/Ferric ratio by using the lab data for total iron and ferrous iron and subtracting to get ferric iron as a concentration in solution. The ferric iron concentration may be combined with flowrate data to obtain the rate of ferric iron applied to the ore. The iron ion ratio may be directly proportional to ORP (a leach variable).

In various embodiments, the system may clean the data using, for example, a set of logical rules. Some logical rules may be based on, for example, statistical outlier calculations or "known logical ranges". The system may also use data interpolation to fill in missing data.

The system may determine (or receive input about) a target amount of daily copper production to obtain from the stockpile. The target may be derived from the predictive model. In various embodiments, the system may determine copper production by comparing flow and grade. The daily copper production may be calculated using daily measurements of flow and copper grade. PLS and raffinate flow are measured in gallons per minute by flow meters. PLS and raffinate copper grade are measured in grams per liter by daily assays. Stockpile production may be calculated by multiplying PLS flow by PLS copper and subtracting the same calculation in the raffinate. The raffinate values are subtracted to avoid double counting copper that was not extracted from the PLS. These four metrics may be observed periodically (e.g., daily) at sumps dedicated to each stockpile, allowing for the periodic calculation of stockpile production.

The system may also obtain data from various tools. In various embodiments, the Mine Material Tracking (MMT) tool may receive data from HPGPS load points, mine data (e.g., from a MineSight system) and/or dispatch data. The HPGPS load points may include Terrain or Provision, along with the HPGPS Loading System that includes dig points. The mine system (e.g., MineSight) may include mine planning software that includes block model files. The dispatch data may include data from a Mine Fleet Management System (FMS) that provides haulage cycle data and/or beacon data. In various embodiments, the MMT tool may link the block model (to get material characteristics) to individual truck loads. The linking may be implemented by interpolating points in the block model because the data from the drill holes may be separated by a sufficient distance (e.g., over 150 feet), so the data from between the holes may need to be interpolated. For example, a first drill hole may include 0.2 copper and a second drill hole may include 0.6 copper, so the system may interpolate the 0.2 amount of copper from the first drill hole up to the 0.6 amount of copper at the second drill hole. Because the drill hole points may have moved after the blast, the system may assign the altered drill hole points to the appropriate physical geographic location post-blast. The system may also merge information from the dispatch tool (the mine fleet management system to get truckload info), CAES and truck sensor data on both haul trucks and shovels (e.g., using ProVision and the GPS coordinates of equipment). The system may then instruct the shovel to take ore from a particular area of the section based on the data indicating where more productive ore and less productive ore may be located.

The MMT tool may allow ore to be tracked from blast to dump at individual truckload locations. The MMT tool may collect and aggregate ore characteristics information at a truckload-by-truckload level. The tool may allow for downstream processes to leverage the block model geologic information, a highly targeted understanding of ore deliveries and locations, and reconciliation of dispatch information with physical processes. The tool may be used for productivity reporting, recovery modeling and other analyses. The MMT tool may also provide data management and data integration functionality to allow mine engineers to review and control the final data output. The MMT tool may provide the users with a much more granular and useful dataset than what may be possible with using only fleet management system data. The MMT tool may integrate with the block model data to provide real-time tracking (e.g., past 24 hours percent TCu deliveries) and improved process modeling and analysis (e.g., past 24 hours percent TClay deliveries).

In various embodiments, the MMT may include SDR (size distribution reporting) to help in obtaining particle size distribution information (e.g., P80) from capturing images of truck loads. The MMT tool may measure SDR data and the SDR data may serve as a predictive variable that contributes to the estimation of stockpile-level copper production via an observational machine learning model.

TROI may be a predictive digital twin model that may use the MMT tool to give real time information about what is going into the crushers, the mine may use the MMT tool to reconcile the geology, and the leaching system may use the MMT tool in the leach analytics.

In various embodiments, the heap concept may include raffinate flow, air and temperature sensors used with the model to make adjustments for optimization. The heap concept may focus on recovery by section/area. The heap concept may maximize as a whole and/or optimize by section. The powerful functionality that leach analytics may provide goes beyond collecting data from various sources into one overarching database. Leach analytics may provide a means for physically understanding how controllable variables impact leach recovery. Going further, leach analytics may provide a means for quantifying complex variable interactions and their collective impact on leach recovery. Therefore, this complete analysis provides the basis of a control strategy such that variables may be changed to optimize an outcome. These changes may be tested manually and then incorporated into interacting automated control systems.

In various embodiments, the mine planning feature may include integration of leaching analytics to mine planning software. The system may make assumptions about the mine production, then create the mine plan. If the system provides assumptions that are more data driven, then the mine plan may be more accurate, economical and productive.

In various embodiments, the system may incorporate drone data or control drones. The drones may survey the stockpile to determine the condition of the stockpile, analyze the stockpile geometry, determine the parts of the stockpile that are being leached, obtain measurements (e.g., heat measurements) and/or transmit that data back to the system.

As will be appreciated by one of ordinary skill in the art, the system may be embodied as a customization of an existing system, an add-on product, a processing apparatus executing upgraded software, a stand-alone system, a distributed system, a method, a data processing system, a device for data processing, and/or a computer program product. Accordingly, any portion of the system or a module may take the form of a processing apparatus executing code, an internet-based embodiment, an entirely hardware embodiment, or an embodiment combining aspects of the internet, software, and hardware. Furthermore, the system may take the form of a computer program product on a computer-readable storage medium having computer-readable program code means embodied in the storage medium.

The system and method may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, lookup tables, and the like, which may carry out a variety of functions under the control of one or more microprocessors or other control devices. Similarly, the software elements of the system may be implemented with any programming or scripting language such as C, C++, C #, JAVA®, JAVASCRIPT®, JAVASCRIPT® Object Notation (JSON), VBScript, Macromedia COLD FUSION, COBOL, MICROSOFT® company's Active Server Pages, assembly, PERL®, PHP, awk, PYTHON®, Visual Basic, SQL Stored Procedures, PL/SQL, any UNIX® shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT®, VBScript, or the like.

In various embodiments, the software elements of the system may also be implemented using a JAVASCRIPT® run-time environment configured to execute JAVASCRIPT® code outside of a web browser. For example, the software elements of the system may also be implemented using NODE.JS® components. NODE.JS® programs may implement several modules to handle various core functionalities. For example, a package management module, such as NPM®, may be implemented as an open source library to aid in organizing the installation and management of third-party NODE.JS® programs. NODE.JS® programs may also implement a process manager, such as, for example, Parallel Multithreaded Machine ("PM2"); a resource and performance monitoring tool, such as, for example, Node Application Metrics ("appmetrics"); a library module for building user interfaces, and/or any other suitable and/or desired module.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the internet server. Middleware may be configured to process transactions between the various components of an application server and any number of internal or external systems for any of the purposes disclosed herein. WEB SPHERE® MQTM (formerly MQSeries) by IBM®, Inc. (Armonk, NY) is an example of a commercially available middleware product. An Enterprise Service Bus ("ESB") application is another example of middleware.

The computers discussed herein may provide a suitable website or other internet-based graphical user interface which is accessible by users. In one embodiment, MICROSOFT® company's Internet Information Services (IIS), Transaction Server (MTS) service, and an SQL SERVER® database, are used in conjunction with MICROSOFT® operating systems, WINDOWS NT® web server software, SQL SERVER® database, and MICROSOFT® Commerce Server. Additionally, components such as ACCESS® software, SQL SERVER® database, ORACLE® software, SYBASE® software, INFORMIX® software, MYSQL® software, INTERBASE® software, etc., may be used to provide an Active Data Object (ADO) compliant database management system. In one embodiment, the APACHE® web server is used in conjunction with a LINUX® operating system, a MYSQL® database, and PERL®, PHP, Ruby, and/or PYTHON® programming languages.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

In various embodiments, the system and various components may integrate with one or more smart digital assistant technologies. For example, exemplary smart digital assistant technologies may include the ALEXA® system developed by the AMAZON® company, the GOOGLE HOME® system developed by Alphabet, Inc., the HOMEPOD® system of the APPLE® company, and/or similar digital assistant technologies.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; financial institution data; and/or like data useful in the operation of the system. As those skilled in the art will appreciate, user computer may include an operating system (e.g., WINDOWS®, UNIX®, LINUX®, SOLARIS®, MACOS®, etc.) as well as various conventional support software and drivers typically associated with computers.

The present system or any part(s) or function(s) thereof may be implemented using hardware, software, or a combination thereof and may be implemented in one or more computer systems or other processing systems. However, the manipulations performed by embodiments may be referred to in terms, such as matching or selecting, which are commonly associated with mental operations performed by a human operator. No such capability of a human operator is necessary, or desirable, in most cases, in any of the operations described herein. Rather, the operations may be machine operations or any of the operations may be conducted or enhanced by artificial intelligence (AI) or machine learning. AI may refer generally to the study of agents (e.g., machines, computer-based systems, etc.) that perceive the world around them, form plans, and make decisions to achieve their goals. Foundations of AI include mathematics, logic, philosophy, probability, linguistics, neuroscience, and decision theory. Many fields fall under the umbrella of AI, such as computer vision, robotics, machine learning, and natural language processing. Useful machines for performing the various embodiments include general purpose digital computers or similar devices. The AI or ML may store data in a decision tree in a novel way.

In various embodiments, the embodiments are directed toward one or more computer systems capable of carrying out the functionalities described herein. The computer system includes one or more processors. The processor is connected to a communication infrastructure (e.g., a communications bus, cross-over bar, network, etc.). Various software embodiments are described in terms of this exemplary computer system. After reading this description, it will become apparent to a person skilled in the relevant art(s) how to implement various embodiments using other computer systems and/or architectures. The computer system can include a display interface that forwards graphics, text, and other data from the communication infrastructure (or from a frame buffer not shown) for display on a display unit.

The computer system also includes a main memory, such as random access memory (RAM), and may also include a secondary memory. The secondary memory may include, for example, a hard disk drive, a solid-state drive, and/or a removable storage drive. The removable storage drive reads from and/or writes to a removable storage unit in a well-known manner. As will be appreciated, the removable storage unit includes a computer usable storage medium having stored therein computer software and/or data.

In various embodiments, secondary memory may include other similar devices for allowing computer programs or other instructions to be loaded into a computer system. Such devices may include, for example, a removable storage unit and an interface. Examples of such may include a program cartridge and cartridge interface (such as that found in video game devices), a removable memory chip (such as an erasable programmable read only memory (EPROM), programmable read only memory (PROM)) and associated socket, or other removable storage units and interfaces, which allow software and data to be transferred from the removable storage unit to a computer system.

In various embodiments, the server may include application servers (e.g., WEB SPHERE®, WEBLOGIC®, JBOSS®, POSTGRES PLUS ADVANCED SERVER®, etc.). In various embodiments, the server may include web servers (e.g., Apache, IIS, GOOGLE® Web Server, SUN JAVA® System Web Server, JAVA® Virtual Machine running on LINUX® or WINDOWS® operating systems).

A web client includes any device or software which communicates via any network, such as, for example any device or software discussed herein. The web client may include internet browsing software installed within a computing unit or system to conduct online transactions and/or communications. These computing units or systems may take the form of a computer or set of computers, although other types of computing units or systems may be used, including personal computers, laptops, notebooks, tablets, smart phones, cellular phones, personal digital assistants, servers, pooled servers, mainframe computers, distributed computing clusters, kiosks, terminals, point of sale (POS) devices or terminals, televisions, or any other device capable of receiving data over a network. The web client may include an operating system (e.g., WINDOWS®, WINDOWS MOBILE® operating systems, UNIX® operating system, LINUX® operating systems, APPLE® OS® operating systems, etc.) as well as various conventional support software and drivers typically associated with computers. The web-client may also run MICROSOFT® INTERNET EXPLORER® software, MOZILLA® FIREFOX® software, GOOGLE CHROME™ software, APPLE® SAFARI® software, or any other of the myriad software packages available for browsing the internet.

As those skilled in the art will appreciate, the web client may or may not be in direct contact with the server (e.g., application server, web server, etc., as discussed herein). For example, the web client may access the services of the server through another server and/or hardware component, which may have a direct or indirect connection to an internet server. For example, the web client may communicate with the server via a load balancer. In various embodiments, web client access is through a network or the internet through a commercially-available web-browser software package. In that regard, the web client may be in a home or business environment with access to the network or the internet. The web client may implement security protocols such as Secure Sockets Layer (SSL) and Transport Layer Security (TLS). A web client may implement several application layer protocols including HTTP, HTTPS, FTP, and SFTP.

The various system components may be independently, separately, or collectively suitably coupled to the network via data links which includes, for example, a connection to an Internet Service Provider (ISP) over the local loop as is typically used in connection with standard modem communication, cable modem, DISH NETWORK®, ISDN, Digital Subscriber Line (DSL), or various wireless communication methods. It is noted that the network may be implemented as other types of networks, such as an interactive television (ITV) network. Moreover, the system contemplates the use, sale, or distribution of any goods, services, or information over any network having similar functionality described herein.

The system contemplates uses in association with web services, utility computing, pervasive and individualized computing, security and identity solutions, autonomic computing, cloud computing, commodity computing, mobility and wireless solutions, open source, biometrics, grid computing, and/or mesh computing.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT® programs, active server pages (ASP), common gateway interface scripts (CGI), extensible markup language (XML), dynamic HTML, cascading style sheets (CSS), AJAX (Asynchronous JAVASCRIPT And XML) programs, helper applications, plug-ins, and the like. A server may include a web service that receives a request from a web server, the request including a URL and an IP address (192.168.1.1). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. For example, representational state transfer (REST), or RESTful, web services may provide one way of enabling interoperability between applications.

Any databases discussed herein may include relational, hierarchical, graphical, blockchain, object-oriented structure, and/or any other database configurations. Any database may also include a flat file structure wherein data may be stored in a single file in the form of rows and columns, with no structure for indexing and no structural relationships between records. For example, a flat file structure may include a delimited text file, a CSV (comma-separated values) file, and/or any other suitable flat file structure. Common database products that may be used to implement the databases include DB2® by IBM® (Armonk, NY), various database products available from ORACLE® Corporation (Redwood Shores, CA), MICROSOFT ACCESS® or MICROSOFT SQL SERVER® by MICROSOFT® Corporation (Redmond, Washington), MYSQL® by MySQL AB (Uppsala, Sweden), MONGODB®, Redis, APACHE CASSANDRA®, HBASE® by APACHE®, MapR-DB by the MAPR® corporation, or any other suitable database product. Moreover, any database may be organized in any suitable manner, for example, as data tables or lookup tables. Each record may be a single file, a series of files, a linked series of data fields, or any other data structure.

As used herein, big data may refer to partially or fully structured, semi-structured, or unstructured data sets including millions of rows and hundreds of thousands of columns. A big data set may be compiled, for example, from a history of purchase transactions over time, from web registrations, from social media, from records of charge (ROC), from summaries of charges (SOC), from internal data, or from other suitable sources. Big data sets may be compiled without descriptive metadata such as column types, counts, percentiles, or other interpretive-aid data points.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); data stored as Binary Large Object (BLOB); data stored as ungrouped data elements encoded using ISO/IEC 7816-6 data elements; data stored as ungrouped data elements encoded using ISO/IEC Abstract Syntax Notation (ASN.1) as in ISO/IEC 8824 and 8825; other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with the system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header," "header," "trailer," or "status," herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the issuer, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, merchant, issuer, user, or the like. Furthermore, the security information may restrict/permit only certain actions, such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer, may be received by a standalone interaction device configured to add, delete, modify, or augment the data in accordance with the header or trailer. As such, in one embodiment, the header or trailer is not stored on the transaction device along with the associated issuer-owned data, but instead the appropriate action may be taken by providing to the user, at the standalone device, the appropriate option for the action to be taken. The system may contemplate a data storage arrangement wherein the header or trailer, or header or trailer history, of the data is stored on the system, device or transaction instrument in relation to the appropriate data.

One skilled in the art will also appreciate that, for security reasons, any databases, systems, devices, servers, or other components of the system may consist of any combination thereof at a single location or at multiple locations, wherein each database or system includes any of various suitable security features, such as firewalls, access codes, encryption, decryption, compression, decompression, and/or the like.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The data may be big data that is processed by a distributed computing cluster. The distributed computing cluster may be, for example, a HADOOP® software cluster configured to process and store big data sets with some of nodes comprising a distributed storage system and some of nodes comprising a distributed processing system. In that regard, distributed computing cluster may be configured to support a HADOOP® software distributed file system (HDFS) as specified by the Apache Software Foundation at www.hadoop.apache.org/docs.

As used herein, the term "network" includes any cloud, cloud computing system, or electronic communications system or method which incorporates hardware and/or software components. Communication among the parties may be accomplished through any suitable communication channels, such as, for example, a telephone network, an extranet, an intranet, internet, point of interaction device (point of sale device, personal digital assistant (e.g., an IPHONE® device, a BLACKBERRY® device), cellular phone, kiosk, etc.), online communications, satellite communications, off-line communications, wireless communications, transponder communications, local area network (LAN), wide area network (WAN), virtual private network (VPN), networked or linked devices, keyboard, mouse, and/or any suitable communication or data input modality. Moreover, although the system is frequently described herein as being implemented with TCP/IP communications protocols, the system may also be implemented using IPX, APPLETALK® program, IP-6, NetBIOS, OSI, any tunneling protocol (e.g. IPsec, SSH, etc.), or any number of existing or future protocols. If the network is in the nature of a public network, such as the internet, it may be advantageous to presume the network to be insecure and open to eavesdroppers. Specific information related to the protocols, standards, and application software utilized in connection with the internet is generally known to those skilled in the art and, as such, need not be detailed herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand.

As used herein, "transmit" may include sending electronic data from one system component to another over a network connection. Additionally, as used herein, "data" may include encompassing information such as commands, queries, files, data for storage, and the like in digital or any other form.

Any database discussed herein may comprise a distributed ledger maintained by a plurality of computing devices (e.g., nodes) over a peer-to-peer network. Each computing device maintains a copy and/or partial copy of the distributed ledger and communicates with one or more other computing devices in the network to validate and write data to the distributed ledger. The distributed ledger may use features and functionality of blockchain technology, including, for example, consensus-based validation, immutability, and cryptographically chained blocks of data. The blockchain may comprise a ledger of interconnected blocks containing data. The blockchain may provide enhanced security because each block may hold individual transactions and the results of any blockchain executables. Each block may link to the previous block and may include a timestamp. Blocks may be linked because each block may include the hash of the prior block in the blockchain. The linked blocks form a chain, with only one successor block allowed to link to one other predecessor block for a single chain. Forks may be possible where divergent chains are established from a previously uniform blockchain, though typically only one of the divergent chains will be maintained as the consensus chain. In various embodiments, the blockchain may implement smart contracts that enforce data workflows in a decentralized manner. The system may also include applications deployed on user devices such as, for example, computers, tablets, smartphones, Internet of Things devices ("IoT" devices), etc. The applications may communicate with the blockchain (e.g., directly or via a blockchain node) to transmit and retrieve data. In various embodiments, a governing organization or consortium may control access to data stored on the blockchain. Registration with the managing organization(s) may enable participation in the blockchain network.

Data transfers performed through the blockchain-based system may propagate to the connected peers within the blockchain network within a duration that may be determined by the block creation time of the specific blockchain technology implemented. For example, on an ETHEREUM®-based network, a new data entry may become available within about 13-20 seconds as of the writing. On a HYPERLEDGER® Fabric 1.0 based platform, the duration is driven by the specific consensus algorithm that is chosen, and may be performed within seconds. In that respect, propagation times in the system may be improved compared to existing systems, and implementation costs and time to market may also be drastically reduced. The system also offers increased security at least partially due to the immutable nature of data that is stored in the blockchain, reducing the probability of tampering with various data inputs and outputs. Moreover, the system may also offer increased security of data by performing cryptographic processes on the data prior to storing the data on the blockchain. Therefore, by transmitting, storing, and accessing data using the system described herein, the security of the data is improved, which decreases the risk of the computer or network from being compromised.

In various embodiments, the system may also reduce database synchronization errors by providing a common data structure, thus at least partially improving the integrity of stored data. The system also offers increased reliability and fault tolerance over traditional databases (e.g., relational databases, distributed databases, etc.) as each node operates with a full copy of the stored data, thus at least partially reducing downtime due to localized network outages and hardware failures. The system may also increase the reliability of data transfers in a network environment having reliable and unreliable peers, as each node broadcasts messages to all connected peers, and, as each block comprises a link to a previous block, a node may quickly detect a missing block and propagate a request for the missing block to the other nodes in the blockchain network.

The particular blockchain implementation described herein provides improvements over conventional technology by using a decentralized database and improved processing environments. In particular, the blockchain implementation improves computer performance by, for example, leveraging decentralized resources (e.g., lower latency). The distributed computational resources improves computer performance by, for example, reducing processing times. Furthermore, the distributed computational resources improves computer performance by improving security using, for example, cryptographic protocols.

The detailed description of various embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not for purposes of limitation. For example, the steps recited in any of the method or process descriptions may be executed in any order and are not limited to the order presented. Moreover, any of the functions or steps may be outsourced to or performed by one or more third parties. Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. Furthermore, any reference to singular includes plural embodiments, and any reference to more than one component may include a singular embodiment. Although specific advantages have been enumerated herein, various embodiments may include some, none, or all of the enumerated advantages.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Although the disclosure includes a method, it is contemplated that it may be embodied as computer program instructions on a tangible computer-readable carrier, such as a magnetic or optical memory or a magnetic or optical disk. All structural, chemical, and functional equivalents to the elements of the above-described various embodiments that are known to those of ordinary skill in the art are expressly incorporated herein by reference and are intended to be encompassed by the present claims. Moreover, it is not necessary for a device or method to address each and every problem sought to be solved by the present disclosure for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. § 112(f) unless the element is expressly recited using the phrase "means for" or "step for". As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. A method of mine material tracking comprising:
receiving, by one or more processors, data, wherein the data comprises terrain data, haul truck sensor data, block model data and dispatch data and at least one of load point data, shovel high-precision global positioning system (HPGPS) data for a shovel, provision data or mine system data;
receiving, by the one or more processors, chemical data and mineralogical data of ore at a plurality of blast holes;
interpolating, by the one or more processors, the plurality of blast holes in the block model data;
assigning, by the one or more processors, the plurality of blast holes to a geographic location post-blast;
merging, by the one or more processors, the geographic location post-blast, the dispatch data, the terrain data and the haul truck sensor data with the block model data;
linking, by the one or more processors, the block model data to a truck load based on the merging;
aggregating, by the one or more processors, ore characteristics for the truck load;
capturing, by the one or more processors, images of ore that is placed in the truck load to determine particle size distribution information about the ore;
determining, by the one or more processors, a location of the ore in a stockpile; and
transmitting, by the one or more processors, to the shovel an instruction signal about the location of the ore in the stockpile having optimal of the ore characteristics to obtain metals from the ore,
wherein the shovel obtains at least a portion of the ore from the location of the ore in the stockpile, in response to the instruction signal.

2. The method of claim 1, further comprising adjusting, by the one or more processors, at least a portion of leaching operations to continue mining production and to optimize the mining production, based on the location of the ore in the stockpile.

3. The method of claim 1, wherein the data comprises the load point data that includes at least one of HPGPS load points or dig point data.

4. The method of claim 1, wherein the data comprises the mine system data that includes at least one of mine planning data or the block model data.

5. The method of claim 1, wherein the dispatch data includes at least one of haulage cycle data or beacon data.

6. The method of claim 1, wherein the haul truck sensor data provides information about the haul trucks.

7. The method of claim 1, further comprising transmitting, by the one or more processors, the location of the ore in the stockpile to a stockpile and section mapping tool.

8. The method of claim 7, wherein the stockpile and section mapping tool provides data to an ore map.

9. The method of claim 8, wherein the ore map provides data to a forecast model input table.

10. The method of claim 7, wherein the stockpile and section mapping tool provides data to a predictive model.

11. An article of manufacture including one or more non-transitory, tangible computer readable storage mediums having instructions stored thereon that, in response to execution by one or more processors, cause the one or more processors processor to perform operations comprising:
receiving, by the one or more processors, data, wherein the data comprises terrain data, haul truck sensor data, block model data and dispatch data and at least one of load point data, shovel high-precision global positioning system (HPGPS) data for a shovel, provision data or mine system data;
receiving, by the one or more processors, chemical data and mineralogical data of ore at a plurality of blast holes;
interpolating, by the one or more processors, the plurality of blast holes in the block model data;
assigning, by the one or more processors, the plurality of blast holes to a geographic location post-blast;
merging, by the one or more processors, the geographic location post-blast, the dispatch data, the terrain data and the haul truck sensor data with the block model data; linking, by the one or more processors, the block model data to a truck load based on the merging;
aggregating, by the one or more processors, ore characteristics for the truck load; capturing, by the one or more processors, images of ore that is placed in the truck load to determine particle size distribution information about the ore;
determining, by the one or more processors, a location of the ore in a stockpile; and
transmitting, by the one or more processors, to the shovel an instruction signal about the location of the ore in the stockpile having optimal of the ore characteristics to obtain metals from the ore,
wherein the shovel obtains at least a portion of the ore from the location of the ore in the stockpile, in response to the instruction signal.

12. A system comprising:
one or more processors; and
one or more tangible, non-transitory memories configured to communicate with the one or more processors,
the one or more tangible, non-transitory memories having instructions stored thereon that, in response to execution by the one or more processors, cause the one or more processors to perform operations comprising:
receiving, by the one or more processors, data, wherein the data comprises terrain data, haul truck sensor data, block model data and dispatch data and at least one of load point data, shovel high-precision global positioning system (HPGPS) data for a shovel, provision data or mine system data;
receiving, by the one or more processors, chemical data and mineralogical data of ore at a plurality of blast holes;
interpolating, by the one or more processors, the plurality of blast holes in the block model data;
assigning, by the one or more processors, the plurality of blast holes to a geographic location post-blast;
merging, by the one or more processors, the geographic location post-blast, the dispatch data, the terrain data and the haul truck sensor data with the block model data;
linking, by the one or more processors, the block model data to a truck load based on the merging;
aggregating, by the one or more processors, ore characteristics for the truck load;
capturing, by the one or more processors, images of ore that is placed in the truck load to determine particle size distribution information about the ore;
determining, by the one or more processors, a location of the ore in a stockpile; and transmitting, by the one or more processors, to the shovel an instruction signal about the location of the ore in the stockpile having optimal of the ore characteristics to obtain metals from the ore, wherein the shovel obtains at least a portion of the ore from the location of the ore in the stockpile, in response to the instruction signal.

13. The system of claim 12, wherein the data comprises the load point data that includes HPGPS load points.

14. The system of claim 12, wherein the data comprises the load point data that includes dig point data.

15. The system of claim 12, wherein the data comprises the mine system data that includes at least one of mine planning data or the block model data.

16. The system of claim 12, wherein the dispatch data includes at least one of haulage cycle data or beacon data.

17. The system of claim 12, wherein the haul truck sensor data provides information about the haul trucks.

18. The system of claim 12, further comprising transmitting, by the one or more processors, the location of the ore in the stockpile to a stockpile and section mapping tool.

19. The system of claim 18, wherein the stockpile and section mapping tool provides data to an ore map.

20. The system of claim 19, wherein the ore map provides data to a forecast model input table.

\* \* \* \* \*